United States Patent
Hoeg-Jensen et al.

(10) Patent No.: US 7,317,000 B2
(45) Date of Patent: *Jan. 8, 2008

(54) GLUCOSE-DEPENDENT INSULINS

(75) Inventors: Thomas Hoeg-Jensen, Klampenborg (DK); Svend Havelund, Bagsvaerd (DK); Jan Markussen, Herlev (DK)

(73) Assignee: Novo Nordisk A/S, Bagsvaerd (DK)

( * ) Notice: Subject to any disclaimer, the term of this patent is extended or adjusted under 35 U.S.C. 154(b) by 167 days.

This patent is subject to a terminal disclaimer.

(21) Appl. No.: 10/307,678

(22) Filed: Dec. 2, 2002

(65) Prior Publication Data

US 2003/0186846 A1 Oct. 2, 2003

Related U.S. Application Data

(60) Provisional application No. 60/337,033, filed on Dec. 5, 2001.

(30) Foreign Application Priority Data

Dec. 2, 2001 (DK) ............................... 2001 01784

(51) Int. Cl.
- *A61K 38/28* (2006.01)
- *C07K 5/00* (2006.01)
- *C07K 7/00* (2006.01)
- *C07K 16/00* (2006.01)
- *C07K 17/00* (2006.01)

(52) U.S. Cl. .......................................... 514/3; 530/303

(58) Field of Classification Search .................. 514/303
See application file for complete search history.

(56) References Cited

U.S. PATENT DOCUMENTS

| 5,478,575 A | 12/1995 | Miyazaki et al. ........... 424/487 |
| 2002/0002876 A1 | 1/2002 | Bezet ........................ 74/594.6 |

FOREIGN PATENT DOCUMENTS

| EP | 0424168 B1 | 10/1990 |
| WO | WO 83/04255 | 12/1983 |
| WO | WO 84/01896 | * 5/1984 |
| WO | WO 99/21888 | 5/1999 |
| WO | WO 00/64940 A1 | 11/2000 |
| WO | WO 01/92334 A1 | 12/2001 |

OTHER PUBLICATIONS

Rudinger. In: Peptide Hormonse, JA Parsons, Ed. 1976, pp. 1-7 and A0.*
SIGMA. Designing Custom Peptides. http://www.sigma-genosys.com/peptide_design.asp (Accessed Dec. 16, 2004). 2 pages.*
Berendsen. A Glimpse of the Holy Grail? Science. 1998. 282. pp. 642-643.*
Voet et al. Biochemistry, 2nd Edition. 1995, pp. 2 covers and 235-241.*
Smilek et al. A single amino acid change in a myelin basic protein peptide confers the capacity to prevent rather than induce experimental autoimmune encephalomyelitis. Proc. Natl. Acad. Sci. USA (1991) 88. pp. 9633-9637.*
Abstract of Japanese Patent JP 2000 086534.
Abstract of Japanese Patent JP 04124144.
Abstract of Japanese Patent JP 04124145.
Brange. Galenics of Insulin. Springer-Verlag. pp. 20-27.
UK Prospective Diabetes Study Group. The Lancet. vol. 352. pp. 854-865 (1998).
Diabetes Control and Complications Trial Research Group, The New England Journal of Medicine. vol. 329. No. 14. pp. 977-987 (1993).
Eggert et al., J. Org. Chem., vol. 64, pp. 3846-3852 (1999).

* cited by examiner

*Primary Examiner*—Cecilia J. Tsang
*Assistant Examiner*—Marcela M Cordero Garcia
(74) *Attorney, Agent, or Firm*—Rosemarie R. Wilk-Orescan

(57) ABSTRACT

The present invention relates to insulin derivatives having a built-in glucose sensor and a polyol moiety, capable to deliver insulin from an injected depot of an insulin derivative according to the invention as a function of the glucose concentration in the surrounding tissue.

29 Claims, 4 Drawing Sheets

GLUCOSE-DEPENDENT INSULINS

CROSS-REFERENCE TO RELATED APPLICATIONS

This application claims priority under 35 U.S.C. 119 of Danish application no. PA 2001/01784 filed Dec. 2, 2001 and U.S. application No. 60/337,033 filed Dec. 5, 2001, the contents of which are fully incorporated herein by reference.

FIELD OF THE INVENTION

The present invention relates to insulin derivatives having a built-in glucose sensor and polyol moiety, capable to deliver insulin from an injected depot as a function of the glucose concentration in the surrounding tissue. Such insulin derivatives are useful in the treatment of diabetes.

In one embodiment of the invention, the insulin derivatives having a built-in glucose sensor and a polyol moiety are integrated in protracted acting, water-soluble aggregates of hexamers of the derivatives in which the propensity to aggregation diminishes, and thereby the rate of absorption of the insulin is increased, as the concentration of glucose in the surrounding medium (e.g. tissue) is increased.

In another embodiment of the invention, crystalline compositions of insulin derivatives having a built-in glucose sensor and a polyol moiety are provided. If the concentration of glucose in the surrounding medium (e.g. tissue) is increased, the rate of dissolution of the insulin crystals is enhanced, and hence the rate of absorption increases.

The invention relates to insulin derivatives having a built-in glucose sensor and a polyol moiety, to pharmaceutical compositions comprising such insulin derivatives capable of releasing insulin as a function of the glucose concentration, and to the use of such compositions in the treatment of diabetes.

BACKGROUND OF THE INVENTION

Diabetes is a disease characterized by an impaired glucose metabolism manifesting itself among other things by an elevated blood glucose level in untreated diabetic patients. The underlying defects lead to a classification of diabetes into two major groups: type 1 diabetes and type 2 diabetes. In type 1 diabetes or insulin demanding diabetes mellitus (IDDM), the patients lack β-cells producing insulin in their pancreatic gland. Type 2 diabetes or non-insulin demanding diabetes mellitus (NIDDM), occurs in patients with an impaired β-cell function besides a range of other abnormalities. Type 2 diabetes may eventually develop into type 1 diabetes. While insulin treatment of patients suffering from type 1 diabetes is indispensable it may also be advantageous in the treatment of type 2 diabetes in some cases.

Since the discovery of insulin in the 1920's, continuous strides have been made to improve the treatment of diabetes mellitus. To help avoid extreme glycaemia levels, diabetic patients often practice multiple injection therapy, whereby insulin is administered with each meal. Many diabetic patients are treated with multiple daily insulin injections in a regimen comprising one or two daily injections of a protracted insulin composition to cover the basal requirement, supplemented by bolus injections of a rapid acting insulin to cover the meal-related requirements.

Insulin compositions having a protracted profile of action are well known in the art. Thus, one main type of such insulin compositions comprises injectable aqueous suspensions of insulin crystals or amorphous insulin. Typically, the insulin in these compositions is provided in the form of protamine insulin, zinc insulin or protamine zinc insulin.

When human or animal insulin is brought to form higher associated forms, e.g. in the presence of $Zn^{2+}$-ions, precipitation in the form of crystals or amorphous product is the result; see, for example, pages 20-27 in Jens Brange (editor), *Galenics of Insulin*, Springer Verlag (1987). Thus, at pH 7, addition of 6 $Zn^{2+}$ ions per insulin hexamer to a solution of porcine insulin will lead to an almost complete precipitation of the insulin.

Another type of protracted insulin compositions can be obtained with insulin analogues that are water soluble at pH values below physiological pH but not at physiological pH. When a solution of such an insulin analogue is injected, the insulin analogue will precipitate to form a subcutaneous depot of solid material because of the rise in the pH value to physiological pH. This principle may be combined with the present invention by incorporation of the glucose-sensor in the insulin analogue. In addition to the glucose sensor these analogues have an amino acid residue in position A21 that is stable at pH values as low as practically useful in solutions to be injected. Examples of suitable amino acid residues at position A21 are glycine, serine and alanine. Also, the insulins have mutations to increase the net charge of the molecule by about 2 units, e.g. Thr in position B27 can be substituted with Arg and Thr-OH in position B30 can be substituted with Thr-$NH_2$ or basic residues can be added, e.g. B31-B32 Arg-Arg.

Soluble insulin derivatives having a lipophilic substituent linked to the ε-amino group of a lysine residue in any of the positions B26 to B30 have been described in the literature. Such derivatives have a protracted profile of action after subcutaneous injection as compared to soluble human insulin, and this protracted action has been explained by a reversible binding to albumin in subcutis, blood and peripheral tissue.

An additional mechanism of prolonging the action of some of the soluble insulin derivatives featuring a lipophilic substituent has been disclosed, i.e. derivatives capable of forming high-molecular-weight aggregates, having a higher molecular weight than aldolase (Mw=158 kDa) when analysed in a specified gel filtration system (WO 99/21888, Novo Nordisk).

In healthy persons, the blood glucose concentration is about 5 mM, rising to about 7 mM after the meals. Today, even when applying the most advanced insulin treatment, using rapid acting insulins for meal-related injections and soluble depot insulin for basal insulin based on frequent monitoring of blood glucose, diabetic patients often experience glucose concentrations out of control. If too much insulin is administered, so that glucose concentrations get below about 3 mM, hypoglycaemic events may occur. When too little insulin is administered and glucose concentrations rises to about 20 mM, acetone appears in the blood and gives rise to diabetic ketoacidosis and, eventually, diabetic coma. In order to avoid these complications and also in order to minimize the occurrence of diabetic late complications it is desirable to control the blood glucose concentration of diabetic patients to be as close to 5 mM as possible. The DCCT (Diabetes Complication Clinical Trial) study from 1993 in USA examined the development of diabetic complications in type 1 diabetic patients during 9 years (N Engl J Med 1993, 329, 977-986). The UKPDS (United Kingdom Prospective Diabetes Study) studied the development of complications in type 2 diabetic patients during 15 years (Lancet 1998, 352, 854-865). Even though the pattern of complications differs between these two types of diabetic patients both investigations conclude that a tight control of blood glucose results in a marked reduction of complications. Thus, there is an unmet need for means to obtain glucose control in diabetic patients closer to the normal value of 5 mM.

In theory, one way to obtain tight glucose control would be to couple a glucose sensor, positioned in the tissue of the patient, to a computer that controls an insulin pump. The pump is via a catheter connected to a needle inserted under the skin. However, it appears as if such a feed back control system has not yet been implemented, possibly because of lack of stable and reliable of glucose sensors. Glucose sensors inserted in the tissue appear to get overgrown with fibrin within a very short time, and it appears that suitable non-invasive sensors, e.g. based on infrared optics, remain to be invented or developed.

Attempts to develop systems for glucose dependent release of insulin from a depot has previously been described. A carbohydrate binding lectin, such as concanavalin A, immobilized to a solid matrix, such as hollow fibres, binds an insulin derivative substituted with a carbohydrate moiety, such as maltotriose, maltose or dextran. The matrix allows diffusion of dissolved glucose and insulin derivative. As the systemic glucose concentration rises, glucose displaces increasing amounts of the insulin derivative from the matrix, thus making more insulin available to the circulation, and thereby to the insulin receptors, when it is needed. It appears as if none of these lectin based systems have been implemented clinically, probably due to the inconvenience of implanting the insulin containing matrix in the body, and to the danger of carrying a large insulin depot within the body.

Another suggested glucose-controlled insulin release system is based on the glucose oxidase catalysed conversion of glucose to gluconic acid. The glucose oxidase is immobilized to a matrix, e.g. of ethylene/vinyl acetate copolymer, and the insulin or insulin derivative is trapped in the matrix in the solid state. As the pH is lowered locally due to the production of gluconic acid the solubility of insulin increases. Thus, the rate of release of soluble insulin from the solid state reflects the glucose concentration. Likewise, it appears as if none of these glucose oxidase based systems have been implemented clinically, possibly for the same reasons.

Furthermore, attempts to provide glucose controlled insulin release from a depot in which the glucose sensing molecular structure is part of a matrix, i.e. a soluble or solid polymer have been made.

SUMMARY OF THE INVENTION

The present invention provides novel insulin derivatives from which the release of insulin from an injected or inhaled depot thereof is glucose dependent. The insulin derivatives are administered to a depot in the body of a diabetic patient in the form of aggregates of hexamers of the insulin derivatives. In the depot, the insulin derivative modified with a glucose sensor and a polyol moiety is either in the crystalline state or in a highly aggregated soluble state. Both states bring about a protracted absorption from the depot. The solubility of the crystals and the state of aggregation of insulin hexamers in the soluble aggregates are influenced by the glucose concentration in the surrounding tissue. Increasing the concentration of glucose promotes dissolution of the crystals and deaggregation of the soluble aggregates of insulin hexamers.

The dose and volume of a subcutaneously or intramuscularly injected depot can be adjusted to be similar to that of the ordinary basal insulin compositions (e.g. NPH insulin), meant to cover basal insulin supply by injection once or twice daily. Doses of compositions for inhalation comprising an insulin derivative according to the present invention may be taken several times during the day, typically before or during meals.

Soluble aggregates of hexamers of insulin derivatives having a lipophilic substituent are disclosed in WO 99/21888 (Novo Nordisk) the contents of which is hereby incorporated in its entirety by reference. The release of insulin derivative from such aggregates appears to depend upon diffusion controlled disintegration of the soluble aggregates.

The high-molecular-weight insulin hexamer aggregates formed by the insulin derivatives according to the present invention deaggregate to form smaller aggregates when glucose is added to a buffer solution containing them. The higher the glucose concentration, the more thorough is the deaggregation of the aggregated derivative.

The state of aggregation and the ability of glucose to reduce the aggregation can be demonstrated by gel filtration of the aggregated insulin derivatives in buffers containing varying concentrations of glucose in the eluents.

The increased release of insulin derivative from subcutaneous depots can be demonstrated by the different levels of the insulin derivative found in the plasma of pigs, rats or mice clamped at various blood glucose levels, e.g. 5 and 10 mM, after injection of the same dose of the insulin derivative.

This new concept of glucose dependent insulin release complies with the convenience of the state of the art injection regimens of insulin therapy, and requires neither surgery nor the danger associated with storage of large implanted depots in the body.

BRIEF DESCRIPTION OF THE DRAWINGS

The present invention is further illustrated with reference to the appended drawings wherein.

| | |
|---|---|
| Vitamin B12 | $10^3$ Dalton |
| $Asp^{B9}Glu^{B27}$ insulin (monomeric) | $6\text{-}10^3$ Dalton |
| Co(III) hexameric insulin | $4\text{-}10^4$ Dalton |
| Human serum albumin | $6\text{-}10^4$ Dalton |
| Blue Dextran | $10^6$ Dalton |

Figure 4:
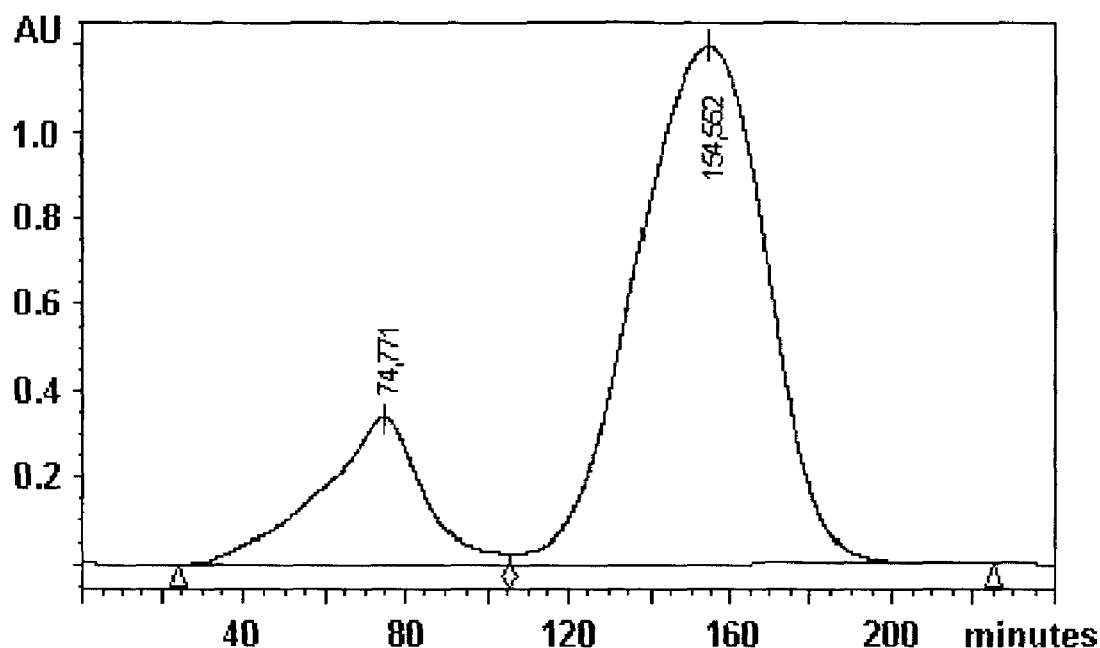

FIG. 4 shows gel filtration analysis of insulin derivative 10 of the present invention, 3 Zn/hexamer with 100 mM NaCl, pH 7.5.

Figure 5:
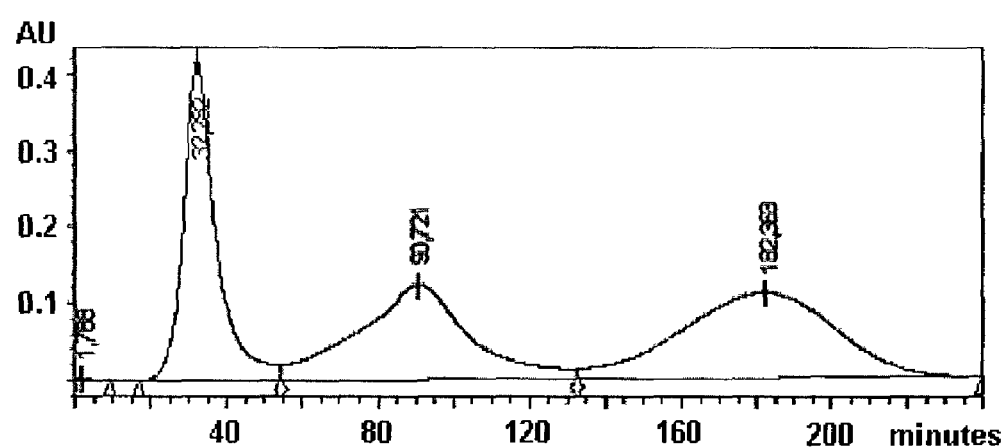

FIG. 5 shows gel filtration analysis of insulin derivative 10 of the present invention, 3 Zn/hexamer with 100 mM NaCl, 6 mM phenol, pH 7.5.

Figure 6:
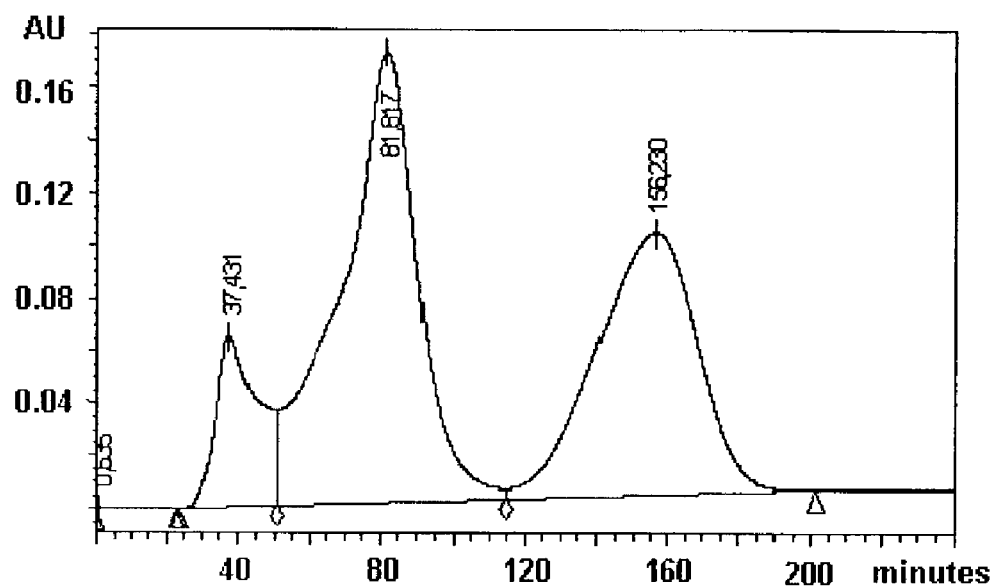

FIG. 6 shows gel filtration analysis of insulin derivative 10 of the present invention, 3 Zn/hexamer with 100 mM NaCl, 6 mM phenol, 20 mM glucose, pH 7.5.

Figure 7:
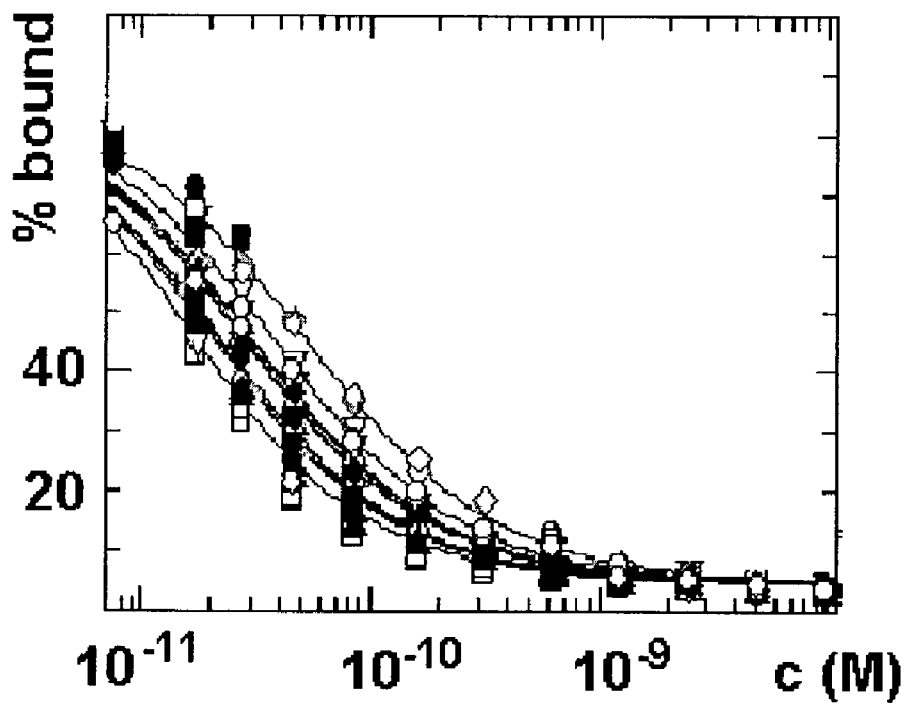

FIG. 7 illustrates human insulin receptor affinities ($K_d$) of insulin derivatives 9 (■), 10 (Δ), 12 (▲), 13 (□), 21 (◇), 23 (□), 27 (○) and 29 (●) of the present invention. (See also Table 1).

DETAILED DESCRIPTION OF THE INVENTION

The expression "insulin derivative" as used herein (and related expressions) refers to human insulin or an analogue thereof in which an organic substituent is bound to at least one of the amino acid residues.

By "analogue of human insulin" as used herein (and related expressions) is meant human insulin in which one or more amino acid residues have been replaced by another amino acid residue or deleted or in which the A chain and/or the B chain has been extended by addition of one or more amino acid residues at the N-terminal or at the C-terminal. "Analogues of human insulin" may be provided by any combination of the above-mentioned modifications of human insulin. While replacements and additions are preferably made with amino acid residues that can be coded for by the genetic code, non-codeable amino acid residues are also an option. In one embodiment of the present invention the insulin analogues are modified in one position only. In other embodiments the insulin analogues are modified at two, three or four positions and the modifications may be in the form of any combination of replacements, deletions and additions. The amino acid sequence of human insulin is given i.a. in The Merck Index, 11th Edition, published in 1989 by Merck & Co., Inc., page 4888.

By a "depot" of insulin is meant a localized amount of subcutaneously or intramuscularly injected insulin or of inhaled insulin, either in the form of a crystalline composition, such as NPH insulin or Lente insulin, or as solutions, such as albumin binding or soluble aggregating or acid solutions of neutral-precipitating insulin analogues or insulin derivatives.

By "absorption" is meant the process by which the insulin in the depot is transferred to the circulation.

By a "polyol moiety" is meant a substituent of the insulin derivative of the invention formed via a covalent bond from a position in the remaining part of the molecule to a polyol, optionally a polyol which further to the OH groups has an amino group or a carboxylic acid group. Examples of polyols are the D- or L-form of glucamine, N-methyl-glucamine, gluconic acid, sorbitol, quinic acid, shikimic acid, inositol, pinitol, tris(hydroxymethyl)aminomethane, pentaerythritol and their derivatives, or derivatives of pentoses and hexoses like glucose, fructose, galactose, mannose or other carbohydrates e.g. derivatives comprising an amino group or a carboxylic acid group.

By "glucose sensor" (in the following also referred to as the boronate moiety) is meant a chemical group capable of binding to or reacting with glucose. The glucose sensor is part of the insulin molecule. For reversible binding, the dissociation constant, $K_d$, of the sensor/glucose complex is usually in the range of from 0.01 μM to 100 mM, for example from 1 μM to 20 mM or from 1 mM to 20 mM or from 1 mM to 100 mM. Examples of reversible glucose sensors are organic borates, preferably aryl boronates or other borates, where the attachment to an insulin derivative is via a carbon-boron bond. Alkyl boronates are oxidatively labile and often unstable (Snyder, Kuck and Johnson, J. Am. Chem. Soc 1938, 60, 105). For use in the present invention, boronate sensors that bind glucose under physiological conditions are preferred. Simple aryl boronates, such as phenyl boronate, bind glucose only at relatively high pH values (pH>9) (Shinkai and Takeuchi, Trends Anal. Chem. 1996, 15, 188). For use in the present invention, acidic boronates that bind glucose at physiological pH values, that is, in the vicinity of pH 7.4, are preferred. Examples of such boronate glucose sensors are aminomethyl-aryl-2-boronates (Bielecki, Eggert and Norrild, J. Chem. Soc., Perkin Trans 2 1999, 449), other boronates with amino groups in the vicinity (Shiino et al, J. Controlled Release 1995, 37, 269), or aryl boronates substituted with electron-withdrawing groups (Eggert et al., J. Org. Chem. 1999, 64, 3846), e.g. sulfo-, carboxy-, nitro-, cyano-, fluoro-phenyl boronates, pyridine boronates, pyridinium boronates or their combinations. Diboronates may be employed to provide glucose selectivity over for instance fructose and lactate. Examples of arylboronate groups that are useful as glucose sensors are shown in formulas A-Z and AA-AE, below. In these formulas, the substituent R in each of the groups designates the insulin moiety of the insulin derivative, including the polyol substituent and an optional linker between the aryl boronate group and the insulin moiety. In formula G, R' designates a substituent selected among the following options: hydrogen, methyl, ethyl, propyl, isopropyl and benzyl. In formula I, R" designates a substituent selected among the following options: D-glucamine, L-glucamine, N-methyl-glucamine, galactamine, N-methyl-galactamine, mannamine, N-methyl-mannamine and tris(hydroxymethyl)amino-methane.

In one embodiment of the present invention, the insulin derivative has the glucose sensor shown in formula A below.

In another embodiment of the present invention, the insulin derivative has the glucose sensor shown in formula B below.

In a further embodiment of the present invention, the insulin derivative has the glucose sensor shown in formula C below.

In a further embodiment of the present invention, the insulin derivative has the glucose sensor shown in formula D below.

In a further embodiment of the present invention, the insulin derivative has the glucose sensor shown in formula E below.

In a further embodiment of the present invention, the insulin derivative has the glucose sensor shown in formula F below.

In a further embodiment of the present invention, the insulin derivative has the glucose sensor shown in formula G below wherein R' designates hydrogen.

In a further embodiment of the present invention, the insulin derivative has the glucose sensor shown in formula G below wherein R' designates a methyl group.

In a further embodiment of the present invention, the insulin derivative has the glucose sensor shown in formula G below wherein R' designates an ethyl group.

In a further embodiment of the present invention, the insulin derivative has the glucose sensor shown in formula G below wherein R' designates a propyl group.

In a further embodiment of the present invention, the insulin derivative has the glucose sensor shown in formula G below wherein R' designates an isopropyl group.

In a further embodiment of the present invention, the insulin derivative has the glucose sensor shown in formula G below wherein R' designates a benzyl group.

In a further embodiment of the present invention, the insulin derivative has the glucose sensor shown in formula H below.

In a further embodiment of the present invention, the insulin derivative has the glucose sensor shown in formula I below wherein R" designates D-glucamine.

In a further embodiment of the present invention, the insulin derivative has the glucose sensor shown in formula I below wherein R" designates L-glucamine.

In a further embodiment of the present invention, the insulin derivative has the glucose sensor shown in formula I below wherein R" designates N-methylglucamine.

In a further embodiment of the present invention, the insulin derivative has the glucose sensor shown in formula I below wherein R" designates galactamine.

In a further embodiment of the present invention, the insulin derivative has the glucose sensor shown in formula I below wherein R" designates N-methylgalactamine.

In a further embodiment of the present invention, the insulin derivative has the glucose sensor shown in formula I below wherein R" designates mannamine.

In a further embodiment of the present invention, the insulin derivative has the glucose sensor shown in formula I below wherein R" designates N-methylmannamine.

In a further embodiment of the present invention, the insulin derivative has the glucose sensor shown in formula I below wherein R" designates tris(hydroxymethyl)aminomethane.

In a further embodiment of the present invention, the insulin derivative has the glucose sensor shown in formula J below.

In a further embodiment of the present invention, the insulin derivative has the glucose sensor shown in formula K below.

In a further embodiment of the present invention, the insulin derivative has the glucose sensor shown in formula L below.

In a further embodiment of the present invention, the insulin derivative has the glucose sensor shown in formula M below.

In a further embodiment of the present invention, the insulin derivative has the glucose sensor shown in formula N below.

In a further embodiment of the present invention, the insulin derivative has the glucose sensor shown in formula O below.

In a further embodiment of the present invention, the insulin derivative has the glucose sensor shown in formula P below.

In a further embodiment of the present invention, the insulin derivative has the glucose sensor shown in formula Q below.

In a further embodiment of the present invention, the insulin derivative has the glucose sensor shown in formula R below.

In a further embodiment of the present invention, the insulin derivative has the glucose sensor shown in formula S below.

In a further embodiment of the present invention, the insulin derivative has the glucose sensor shown in formula T below.

In a further embodiment of the present invention, the insulin derivative has the glucose sensor shown in formula U below.

In a further embodiment of the present invention, the insulin derivative has the glucose sensor shown in formula V below.

In a further embodiment of the present invention, the insulin derivative has the glucose sensor shown in formula Y below.

In a further embodiment of the present invention, the insulin derivative has the glucose sensor shown in formula X below.

In a further embodiment of the present invention, the insulin derivative has the glucose sensor shown in formula Z below.

In a further embodiment of the present invention, the insulin derivative has the glucose sensor shown in formula AA below.

In a further embodiment of the present invention, the insulin derivative has the glucose sensor shown in formula AB below.

In a further embodiment of the present invention, the insulin derivative has the glucose sensor shown in formula AC below.

In a further embodiment of the present invention, the insulin derivative has the glucose sensor shown in formula AD below.

In a further embodiment of the present invention, the insulin derivative has the glucose sensor shown in formula AE below.

-continued
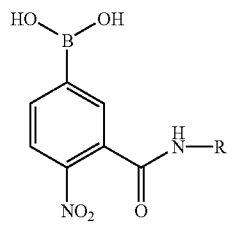 E
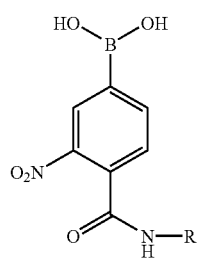 F
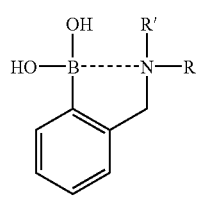 G
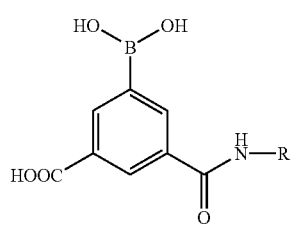 H
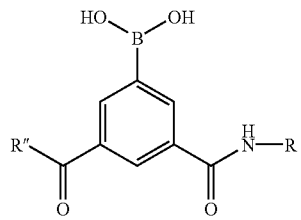 I
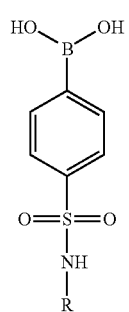 J
-continued
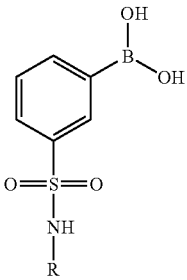 K
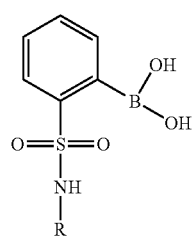 L
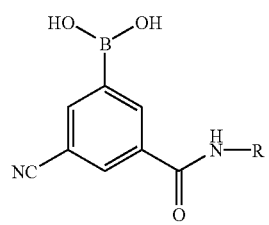 M
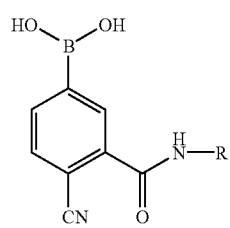 N
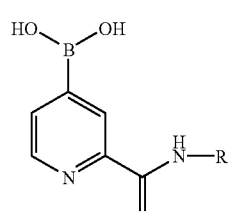 O
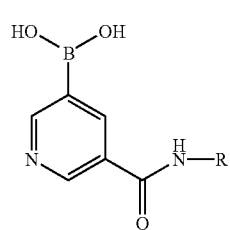 P

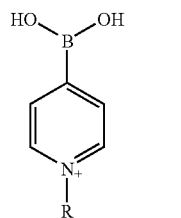
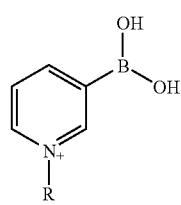
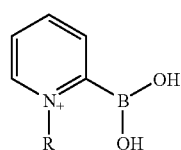
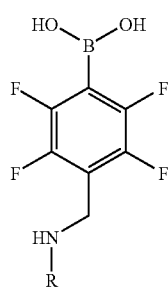
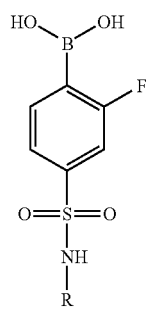
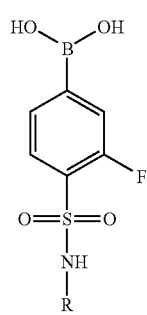
Q
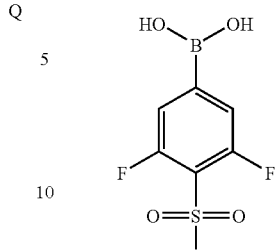
R
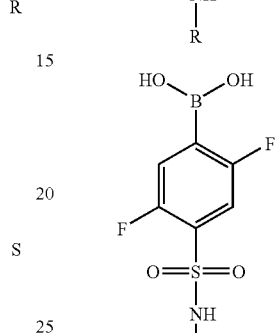
S
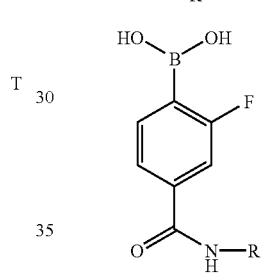
T
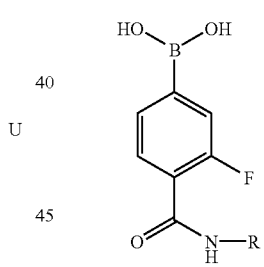
U
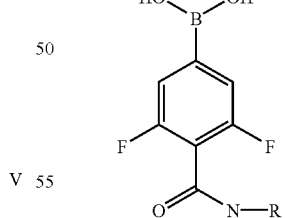
V
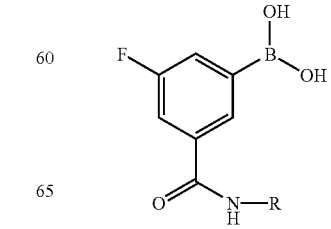

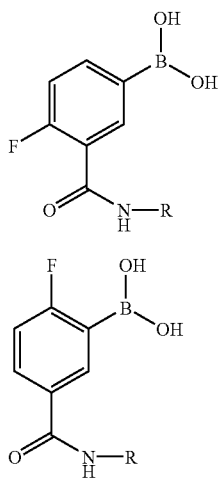

Such acidic boronates assume a tetrahedral configuration in aqueous solvent at physiological pH, thereby allowing binding of glucose. Reversible glucose sensors may also be peptides or pseudopeptides, optionally containing boronates. In a further embodiment, heteroaryl boronates based on heterocyclic rings like pyridine or thiophene can be used as glucose sensors.

In one embodiment of the present invention there are provided soluble and aggregated hexamers of insulin derivatives, wherein the state of aggregation is dependent on the amount of glucose present. The aggregated insulin derivatives are soluble in water at physiological pH values, that is around pH 7.4, and are also useful in a broader pH range, for example in the range from 6.8 to 8.5. The soluble, aggregated hexamers of insulin derivatives deaggregate slowly after subcutaneous injection, making them suitable for used in long-acting insulin compositions, the advantage being that such compositions will contain no precipitate. The higher the concentration of glucose is in the tissue surrounding the injection site is, the higher the rate of deaggregation of an injected aggregated insulin derivative will be and the higher the rate of the subsequent absorption of the insulin derivative will be. The advantage of having an insulin composition that is a solution rather than a suspension is that more precise doses can be given, there is no need to shake of the vial or pen before a dose is given, a thinner injection needle can be used and thus the injection causes less pain, it is easier to fill the vials or cartridges and no ball is needed in the cartridge since there is no precipitate to be suspended.

The apparent volume of elution of aggregates of insulin hexamers, as estimated by the distribution coefficient, $K_{AV}$, changes to a higher value when the glucose concentration is increased from 0 to 20 mM or to 100 mM, as determined by gel filtration using a Bio-Gel P300 (BIO-RAD). In order to achieve an optimal effect of glucose on the state of aggregation in this experiment, the concentration of sodium chloride should be decreased just to obtain an aggregation about the size of aldolase (i.e. the $K_{AV}$ value of 0.10).

The aggregated form can be observed for insulin derivatives under conditions where the hexameric unit is known to exist for most natural insulins. Thus, in a preferred embodiment, the aggregated form is composed of hexameric subunits, preferably of at least 4, more preferred 5 to 500, hexameric subunits. Any hexameric subunit of the aggregated forms of the compounds of this invention may have any of the known $R_6$, $R_3T_3$, or $T_6$ structures, $T_6$ being the preferred form (Kaarsholm, Biochemistry 28, 4427-4435, 1989).

Substances like $Zn^{2+}$ known to stabilise the hexameric unit are also found to stabilise the aggregated form of some insulin derivatives. The building blocks forming the aggregates may be the hexameric units known from the X-ray crystallographic determined structure of insulin (Blundell, Diabetes 21 (Suppl. 2), 492-505, 1972). Ions like $Zn^{2+}$, known to stabilise the hexameric unit as 2 or 4 $Zn^{2+}$/hexamer complexes (Blundell, Diabetes 21 (Suppl. 2), 492-505, 1972), are essential for the formation of aggregates for most insulin analogues and derivatives. Thus, compositions of glucose dependent aggregating insulin derivatives according to this invention preferably comprise at least 2 zinc ions, more preferred 2 to 5 zinc ions, for example 3 or 4 zinc ions, still more preferred 2.5 to 3.5 zinc ions, per 6 molecules of monomeric insulin derivative. Moreover, the compositions advantageously comprise at least 3 molecules of a phenolic compound, like phenol or a cresol, especially m-cresol, per 6 molecules of insulin derivative. In the central cavity of the 2 $Zn^{2+}$/hexamer structure 6 residues of $Glu^{B13}$ provide binding sites for up to 3 $Ca^{2+}$ ions (Sudmeier et al., Science 212, 560-562, 1981). Thus, addition of $Ca^{2+}$ ions stabilises the hexamer and may be added to the pharmaceutical compositions, provided that the insulin derivative remains in solution.

The disappearance half-time of the insulin aggregates of the invention after subcutaneous injection in healthy human subjects, having normal blood glucose concentrations about 5 mM, is as long as or longer than that of a human insulin NPH composition.

In one particular embodiment of the present invention, the aggregate is composed of insulin derivatives, which have an albumin binding which is lower than that of $Lys^{B29}(N^\epsilon$-tetradecanoyl) des(B30) human insulin.

The substituent at the lysine residue of the insulin derivatives of the aggregate according to the invention is preferably a group incorporating a boronate moiety and a polyol moiety. The boronate moiety and the polyol moiety are then kept apart by a scaffold that prevents the boronate moiety and the polyol moiety from binding internally in the insulin monomer. However, the boronate moiety and the polyol moiety may also be coupled to each their own amino acid residue of the insulin moiety.

In one embodiment, insulin derivatives of the invention have the arylboronate group (glucose sensor) attached to the insulin moiety via the α-amino group of the N-terminal amino acid residue of the A chain or the B chain or via the ε-amino group of a Lys residue at position B3, B28, B29 or B30 or a Orn residue, a Dap residue, a Dab residue, an Asp residue or a Glu residue at position B30.

In one particular form of this embodiment, insulin derivatives of the invention have the arylboronate group attached to the insulin moiety via the α-amino group of the N-terminal amino acid residue of the A chain.

In another particular form of this embodiment, insulin derivatives of the invention have the arylboronate group attached to the insulin moiety via the α-amino group of the N-terminal amino acid residue of the B chain.

In another particular form of this embodiment, insulin derivatives of the invention have the arylboronate group attached to the insulin moiety via the ε-amino group of a Lys residue at position B3.

In another particular form of this embodiment, insulin derivatives of the invention have the arylboronate group attached to the insulin moiety via the ε-amino group of a Lys residue at position B28.

In another particular form of this embodiment, insulin derivatives of the invention have the arylboronate group attached to the insulin moiety via the ε-amino group of a Lys residue at position B29.

In another particular form of this embodiment, insulin derivatives of the invention have the arylboronate group attached to the insulin moiety via the ε-amino group of a Lys residue at position B30.

In another particular form of this embodiment, insulin derivatives of the invention have the arylboronate group attached to the insulin moiety via an Orn residue at position B30.

In another particular form of this embodiment, insulin derivatives of the invention have the arylboronate group attached to the insulin moiety via a Dap residue at position B30.

In another particular form of this embodiment, insulin derivatives of the invention have the arylboronate group attached to the insulin moiety via a Dab residue at position B30.

In another particular form of this embodiment, insulin derivatives of the invention have the arylboronate group attached to the insulin moiety via an Asp residue at position B30.

In another particular form of this embodiment, insulin derivatives of the invention have the arylboronate group attached to the insulin moiety via a Glu residue at position B30.

In another embodiment, insulin derivatives of the invention have the arylboronate group (glucose sensor) attached to the insulin moiety via a linker. Examples of suitable linkers for this purpose comprise γ-glutamyl, α-glutamyl, β-aspartyl, α-aspartyl, β-alanine, 4-carboxy-phenylalanine, iminodiacetic acid, piperazine and aniline.

In one particular form of this embodiment, insulin derivatives of the invention have the arylboronate group attached to the insulin moiety via a linker which is γ-glutamyl.

In one particular form of this embodiment, insulin derivatives of the invention have the arylboronate group attached to the insulin moiety via a linker which is α-glutamyl.

In one particular form of this embodiment, insulin derivatives of the invention have the arylboronate group attached to the insulin moiety via a linker which is β-aspartyl.

In one particular form of this embodiment, insulin derivatives of the invention have the arylboronate group attached to the insulin moiety via a linker which is α-aspartyl.

In one particular form of this embodiment, insulin derivatives of the invention have the arylboronate group attached to the insulin moiety via a linker which is β-alanine.

In one particular form of this embodiment, insulin derivatives of the invention have the arylboronate group attached to the insulin moiety via a linker which is 4-carboxyphenylalanine.

In one particular form of this embodiment, insulin derivatives of the invention have the arylboronate group attached to the insulin moiety via a linker which is iminodiacetic acid.

In one particular form of this embodiment, insulin derivatives of the invention have the arylboronate group attached to the insulin moiety via a linker which is piperazine.

In one particular form of this embodiment, insulin derivatives of the invention have the arylboronate group attached to the insulin moiety via a linker which is aniline.

In a further embodiment of the invention, the glucose-sensing aryl boronate group is a part of the amino acid residue in position B26 of the insulin moiety.

In a further embodiment of the invention, the glucose-sensing group is built into a substituent capable of effecting the formation of high-molecular-weight aggregates.

In a further embodiment of the invention, the glucose-sensing group is an aryl boronate, causing aggregation by binding to a polyol moiety in a neighbouring molecule.

In a further embodiment of the invention, insulin derivatives of the invention have the polyol moiety attached to the insulin moiety via the ε-amino group of the N-terminal amino acid residue of the A chain or the B chain or via the ε-amino group of a Lys residue at position B3, B28, B29 or B30 or a Orn residue, a Dap residue, a Dab residue, an Asp residue or a Glu residue at position B30.

In one particular form of this embodiment, insulin derivatives of the invention have the polyol moiety attached to the insulin moiety via the α-amino group of the N-terminal amino acid residue of the A chain.

In another particular form of this embodiment, insulin derivatives of the invention have the polyol moiety attached to the insulin moiety via the α-amino group of the N-terminal amino acid residue of the B chain.

In another particular form of this embodiment, insulin derivatives of the invention have the polyol moiety attached to the insulin moiety via the ε-amino group of a Lys residue at position B3.

In another particular form of this embodiment, insulin derivatives of the invention have the polyol moiety attached to the insulin moiety via the ε-amino group of a Lys residue at position B28.

In another particular form of this embodiment, insulin derivatives of the invention have the polyol moiety attached to the insulin moiety via the ε-amino group of a Lys residue at position B29.

In another particular form of this embodiment, insulin derivatives of the invention have the polyol moiety attached to the insulin moiety via the ε-amino group of a Lys residue at position B30.

In another particular form of this embodiment, insulin derivatives of the invention have the polyol moiety attached to the insulin moiety via an Orn residue at position B30.

In another particular form of this embodiment, insulin derivatives of the invention have the polyol moiety attached to the insulin moiety via a Dap residue at position B30.

In another particular form of this embodiment, insulin derivatives of the invention have the polyol moiety attached to the insulin moiety via a Dab residue at position B30.

In another particular form of this embodiment, insulin derivatives of the invention have the polyol moiety attached to the insulin moiety via an Asp residue at position B30.

In another particular form of this embodiment, insulin derivatives of the invention have the polyol moiety attached to the insulin moiety via a Glu residue at position B30.

In a further embodiment, insulin derivatives of the invention have the polyol moiety attached to the insulin moiety via a linker. Examples of suitable linkers for this purpose comprise γ-glutamyl, α-glutamyl, β-aspartyl, α-aspartyl, β-alanine, 4-carboxyphenylalanine, iminodiacetic acid, piperazine and aniline.

In one particular form of this embodiment, insulin derivatives of the invention have the polyol moiety attached to the insulin moiety via a linker which is γ-glutamyl.

In one particular form of this embodiment, insulin derivatives of the invention have the polyol moiety attached to the insulin moiety via a linker which is α-glutamyl.

In one particular form of this embodiment, insulin derivatives of the invention have the polyol moiety attached to the insulin moiety via a linker which is β-aspartyl.

In one particular form of this embodiment, insulin derivatives of the invention have the polyol moiety attached to the insulin moiety via a linker which is α-aspartyl.

In one particular form of this embodiment, insulin derivatives of the invention have the polyol moiety attached to the insulin moiety via a linker which is β-alanine.

In one particular form of this embodiment, insulin derivatives of the invention have the polyol moiety attached to the insulin moiety via a linker which is 4-carboxyphenylalanine.

In one particular form of this embodiment, insulin derivatives of the invention have the polyol moiety attached to the insulin moiety via a linker which is iminodiacetic acid.

In one particular form of this embodiment, insulin derivatives of the invention have the polyol moiety attached to the insulin moiety via a linker which is piperazine.

In one particular form of this embodiment, insulin derivatives of the invention have the polyol moiety attached to the insulin moiety via a linker which is aniline.

When both the aryl boronate moiety and the polyol moiety are attached to the insulin moiety via a linker they can be attached to the same linker.

An example of a useful scaffold or linker to which both the glucose sensing boronate moiety and the polyol moiety can be attached is the γ-Glu linker used in the present examples 1 to 4.

The present invention furthermore provides novel insulin derivatives capable of forming aggregates, in which the state of aggregation is inversely correlated to the glucose concentration. These insulin derivatives may be provided in the form of aggregates in pharmaceutical compositions or, alternatively, they may be provided in a non-aggregated form in pharmaceutical compositions, in which case the aggregates form after subcutaneous injection of said compositions.

Figure 1:
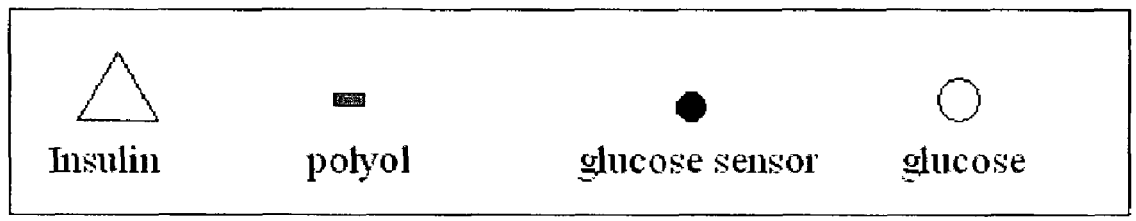
FIG. 1 shows in a schematic way a small aggregate of hexamers of an insulin derivative according to the invention and its disintegration in the presence of glucose.
Figure 1:
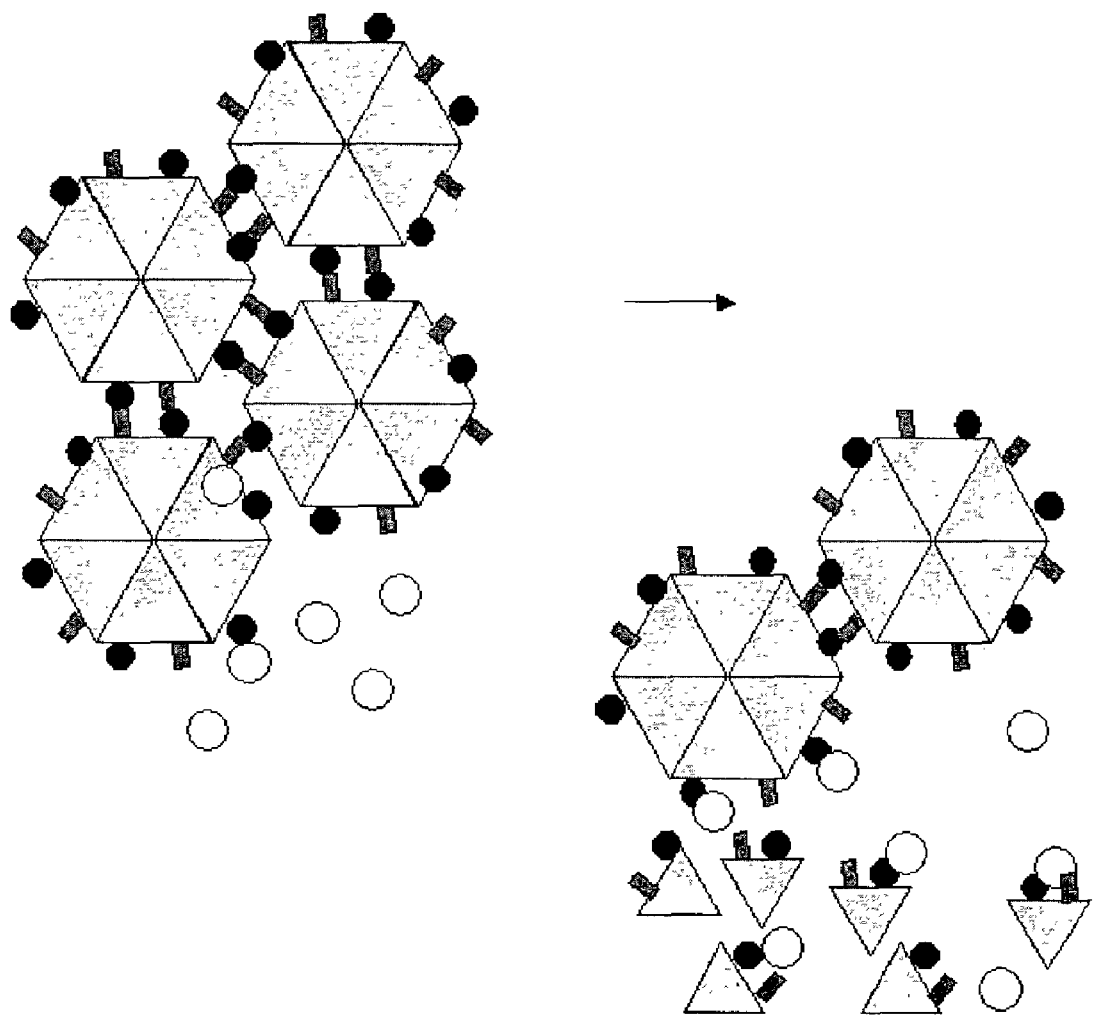
Figure 2:
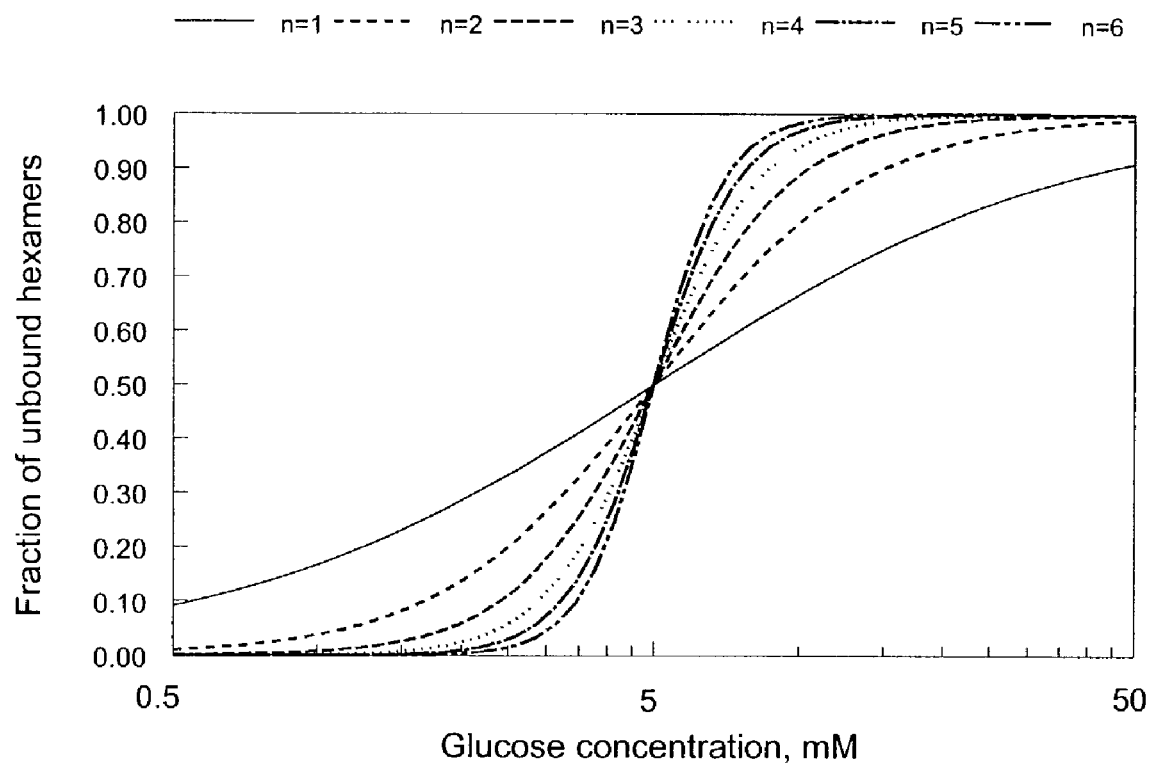
FIG. 2 shows that a steep correlation between the release of insulin and the glucose concentration is possible by the multiple interactions between insulin hexamers as compared to a mechanism involving just one bond.
Figure 3:
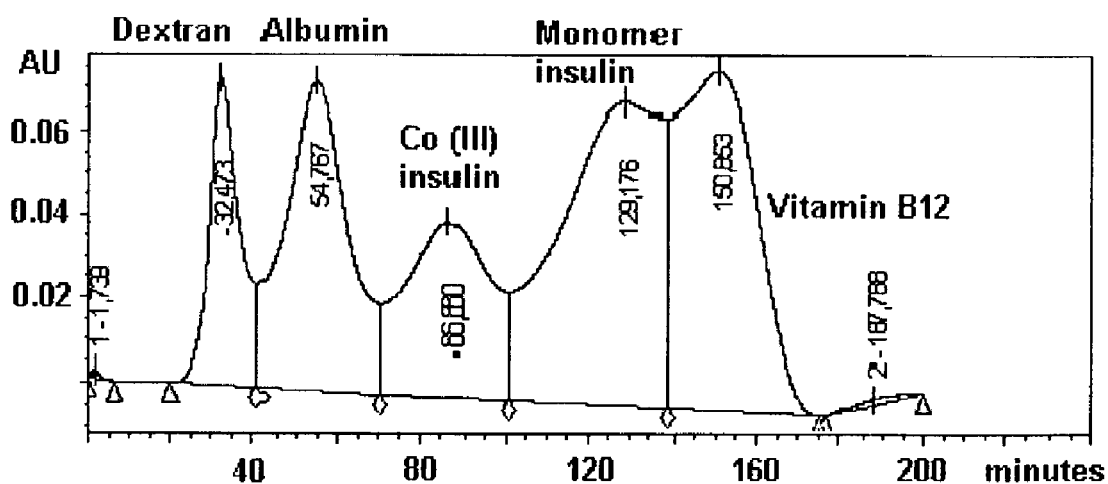
FIG. 3 shows gel filtration standards in the molecular weight range $10^3$ to $10^6$ Daltons.

Accordingly, the present invention furthermore is concerned with pharmaceutical compositions comprising an aggregate of insulin derivatives or non-aggregated insulin derivatives, which form aggregates after subcutaneous injection, the degree of aggregation being inversely correlated to the glucose concentration. The dissociation of the soluble insulin polymers (i.e. aggregates of insulin hexamers) into soluble insulin hexamers by the action of glucose molecules can be described by the following equation:

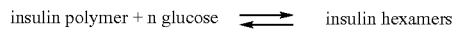

insulin polymer + n glucose ⇌ insulin hexamers where n is the number of glucose molecules required to break the polymeric insulin network, releasing the insulin hexamers from the network. The advantage of n being larger than 1 is apparent from FIG. 2, which shows that increasing n from 1 to 6 increases the steepness of the curve for the fraction of free insulin hexamers over polymer, bound insulin hexamers. Thus, a faster release of insulin at a high glucose concentration, and a slower release at a low glucose concentration, is possible by the multiple interactions between insulin hexamers than by a mechanism involving just one bond.

Preferably, the pharmaceutical composition according to the present invention comprises aggregates of insulin hexamers, a substantial fraction of which aggregates have a molecular weight higher than the molecular weight of aldolase as determined by gel filtration using the medium of the composition as eluent.

In one embodiment according to the invention, a pharmaceutical composition of an insulin is provided in which at least 50% by weight of the glucose sensing insulin contained in the composition is present in the form of aggregates of hexamers.

In another embodiment of the invention, a pharmaceutical composition is provided which comprises both an aggregating insulin derivative according to the present invention (i.e. an insulin derivative having a protracted profile of action) and a rapid acting insulin analogue, the latter preferably being human insulin or one of the insulin analogues Asp$^{B28}$ human insulin, Lys$^{B28}$Pro$^{B29}$ human insulin, Lys$^{B3}$Glu$^{B29}$ human insulin, Gly$^{A21}$Lys$^{B3}$Glu$^{B29}$ human insulin, Asp$^{A21}$Lys$^{B3}$Glu$^{B29}$ human insulin, GlyA21Lys$^{B3}$Ile$^{B28}$ human insulin, Asp$^{A21}$Lys$^{B3}$Ile$^{B28}$ human insulin or des (B30) human insulin. Such a composition will provide both a rapid onset of action and a prolonged profile of action, the latter being influenced by the blood glucose concentration of the diabetic patient. In case the two insulins of the mixture form mixed hexamers both will be under influence of the blood glucose concentration. In this embodiment, the pharmaceutical composition preferably comprises aggregating insulin and rapid acting insulin in a molar ratio of from 90:10 to 10:90.

The slow dissociation of the aggregated insulin derivatives may be further slowed down in vivo by the addition of physiologically acceptable agents that increase the viscosity of the pharmaceutical composition. Thus, the pharmaceutical composition according to the invention may furthermore comprise an agent that increases the viscosity, for example selected from the group comprising polyethylene glycol, polypropylene glycol, copolymers thereof, dextrans and/or polylactides.

In yet another embodiment of the present invention; an insulin derivative having a glucose sensing group and a polyol moiety is prepared as a crystalline NPH composition, using protamine to form the crystals, or as a crystalline Lente composition, using Zn$^{2+}$-ions in the crystals. In these cases the rate of dissolution of the crystals is enhanced by the interaction between glucose and the glucose-sensing group.

In yet another embodiment, the protracted insulin compositions are solutions having a pH value below physiological pH from which the insulin analogue will precipitate because of the rise in the pH value to physiological pH when the solution has been injected. Such analogues are described in EP 0 254 516 B1 (Novo Nordisk) and EP 0 368 187 B1 (Hoechst). These analogues have an amino acid residue in position A21 that is stable at pH values as low as practically useful in solutions to be injected. Examples of suitable amino acid residues at position A21 are glycine, serine or alanine. Also, the insulins have mutations to increase the net charge of the molecule by about 2, e.g. Thr in position B27 can be substituted with Arg and Thr-OH in position B30 can be substituted with Thr-NH$_2$ or have additional basic residues, e.g. B31-B32 Arg-Arg. When this principle is combined with the present invention by incorporation of the glucose-sensor and a polyol moiety in these insulin analogues, the solubility of the crystals is enhanced by the interaction between glucose and the glucose-sensing group, facilitating the absorption.

Sites enabling the attachment of a glucose sensor and a polyol moiety are the N-terminal amino groups of glycine A1 and phenylalanine B1 and the ε-amino group of lysine B29. In analogues of human insulin one or more additional or alternative lysine residues may be incorporated for this purpose, e.g. in position B3 or B28. Furthermore the glucose sensor may be incorporated as part of the peptide chain, preferably in the C-terminal part of the B-chain.

Pharmaceutical Compositions

Pharmaceutical compositions containing an insulin derivative according to the present invention may further comprise a buffer substance, such as a phosphate, for example sodium phosphate, glycine or glycylglycine buffer, an isotonicity agent, such as sodium chloride, dimethylsulphone or glycerol, and phenol and/or m-cresol as a preservative. Optionally, mannitol or sorbitol can be added and the resulting interaction with the glucose sensor can be utilized to adjust stability and the release profile of the composition. Among the auxiliary substances of a pharmaceutical composition according to the present invention, the sodium chloride, used as isotonic agent, the zinc- and optionally calcium ions, which promote and stabilize the hexamer formation, are particularly important since they facilitate the aggregation of the insulin derivative in the composition and thereby effectively prolong the time of disappearance from the site of injection. A pharmaceutical composition according to the invention preferably comprises chloride ions in a concentration of 5 to 150 mM.

In pharmaceutical compositions, the concentration of the glucose-sensing insulins of the present invention is generally in the range from 0.1 to 15 mM for example from 0.1 to 2 mM. The amount of zinc contained in the compositions is 0.3-0.9% by weight relative to the insulin derivative. Phenolic compounds like phenol or m-cresol or mixtures thereof are suitably applied in a total concentration of from 5 to 50 mM, and chloride ions in a concentration of from 10 mM to 120 mM.

The present invention furthermore relates to a method of treating diabetes mellitus comprising administering to a person in need of such treatment an effective amount of water-soluble aggregates of insulin derivatives according to the invention or effective amount an insulin derivative according to the invention, capable of forming water-soluble aggregates upon subcutaneous injection, aggregate size depending on the glucose concentration.

The optimal dose level for any patient will depend on a variety of factors including the efficacy of the specific human insulin derivative employed, the age, body weight, physical activity, and diet of the patient, on a possible combination with other drugs, and on the severity of the case of diabetes. It is recommended that the daily dosage of the human insulin derivative of this invention be determined for each individual patient by those skilled in the art in a similar way as for known insulin compositions.

The glucose sensor and polyol building blocks used in preparation of the glucose-sensing insulins can be prepared as described in the included examples. The insulin derivatives of the invention can be prepared by the general methods disclosed in WO 95/07931 (Novo Nordisk A/S), WO 96/00107 (Novo Nordisk A/S), WO 97/31022 (Novo Nordisk A/S), WO098/02460 (Novo Nordisk A/S), EP 511 600 (Kuraray Co. Ltd.) and EP 712 862 (Eli Lilly).

Determination of Insulin Receptor Binding

The insulin activity of the insulin derivatives of the invention can be demonstrated by their binding to an insulin receptor preparation. Scintiplates (Wallac) are coated with Goat antimouse IgG and an insulin receptor antibody is added, followed by solubilized human insulin receptor. The binding of the insulins of the invention to the insulin receptor is measured by competition with $^{125}$I-TyrA14 human insulin and scintillation counting. Results for examples of the invention are presented in Table 1.

TABLE 1

| Compound No. | Insulin receptor K$_d$ (pM) |
|---|---|
| Human insulin | 11 |
| 9 | 15 |
| 10 | 16 |
| 12 | 10 |
| 13 | 20 |
| 21 | 29 |
| 23 | 15 |
| 27 | 16 |
| 29 | 11 |

Determination of Aggregate Formation

The aggregated form of the insulins of the invention is demonstrated by gel filtration using a gel with an exclusion limit higher than or equal to aldolase. An aqueous buffer system at neutral pH is used in the gel filtration and the insulin derivatives are applied to the column in the form of a pharmaceutical composition at a concentration of 600 nmol insulin/ml. Insulin derivatives in the aggregated state elute together with or before aldolase, which has a molecular weight of 158 kDa.

The elution volume of a gel filtration can be described by the distribution coefficient, $K_{AV}$, defined as $$K_{AV} = (V_R - V_0)/(V_t - V_0)$$

where $V_R$ is retention volume, $V_0$ is void volume and $V_t$ the total volume of the bed. $V_0$ is obtained as the elution volume of blue dextran and $V_t$ by measuring the column dimensions and calculation of the volume.

The gel filtration experiment using the conditions prescribed in this section is a direct physicochemical method, which can be used to demonstrate the aggregate forming properties of the insulin derivatives of the present invention. The rate at which an insulin derivative disappears from the injection site after subcutaneous injection reflects the combined influence of the polymer formation, the glucose concentration and the albumin binding properties of the insulin derivative, besides a variety of biological factors. A convenient measure of the disappearance rate is the disappearance half-life, $T_{50\%}$, which can be measured e.g. in pigs. $T_{50\%}$ is the time when 50% of the A14 Tyr($^{125}$I) analogue has disappeared from the site of injection as measured with an external γ-counter (Ribel, U et al., The Pig as a Model for Subcutaneous Absorption in Man. In: M. Serrano-Rios and P. J. Lefebre (Eds): Diabetes 1985; Proceedings of the 12th Congress of the International Diabetes Federation, Madrid, Spain, 1985 (Excerpta Medica, Amsterdam, (1986) 891-96).

The formation of glucose-dependent, high-molecular-weight, soluble aggregates may be demonstrated by gel filtration using a column of the polyacrylamide gel Bio-Gel P300 (BIO-RAD) in a neutral aqueous eluent comprising from 20 to 140 mM sodium chloride, 5 mM sodium phosphate at pH 7.4 or higher and a glucose concentration varying from 0 to 20 mM or higher, e.g. from 0 to 100 mM. For insulin derivatives eluting partly after the column volume the gel filtration may be performed with a lower sodium chloride concentration. The buffer system described was chosen to mimic the conditions in mammalian tissue in vivo, in order to be able to detect derivatives changing their state of aggregation under conditions similar to those after the subcutaneous injection. In other buffer systems, decreasing the concentration of sodium chloride, or increasing the pH value precisely to obtain aggregates having a molecular weight close to the molecular weight of aldolase, the possibility of observing glucose influence is better.

Gel filtration assay for aggregation: An empty column HR 10/10 (Amersham Pharmacia Biotech code 19-7402-01) useable for 10×1 cm column and with low dead volume was packed with Bio-Gel P-300 (BIO-RAD) according to the instruction manual (BIO-RAD) and eluted at a linear flow of 4.5 cm/h (0.06 ml/min) at 37° C. The actual column length of about 10 cm was measured to calculate the total bed volume. A 7.9 ml gel filtration column useable for separation of a wide molecular weight range, Bio-Gel 300 (BIORAD), was eluted at 37° C. by sodium chloride 100 mM, sodium phosphate 5 mM, preserved with sodium azide 0.01% and hydrochloric acid added to pH 7.4. Run time was 240 min and injection volume was 100 µl. For insulin derivatives eluting partly after the column volume the gel filtration was repeated with a lower sodium chloride concentration. The dissociation effect of glucose on the state of aggregation was tested by inclusion of glucose 20 mM or higher and optionally increasing the pH to 8.0.

Alternative methods to study the state of aggregation are light scattering, osmometry and ultra centrifugation.

EXAMPLES

Acronyms Used for Chemical Groups and Commercially Available Chemicals:

| | |
|---|---|
| Boc | tert-Butoxycarbonyl |
| Bzl | Benzyl |
| Dab | Diaminobutyric acid |
| Dap | Diaminopropionic acid |
| DCC | N,N'-Dicyclohexylcarbodiimide |
| DCM | Dichloromethane |
| DIEA | N,N-Diisopropylethylamine |
| DMF | N,N-Dimethylformamide |
| DMSO | Dimethyl sulfoxide |
| Glu | Glutamic acid |
| HATU | 7-Azabenzotriazol-1-yl-oxy-tetramethyluronium hexafluorophosphate |
| HOSu | N-Hydroxysuccinimide |
| TBTU | Benzotriazol-1-yl-oxy-tetramethyluronium tetrafluoroborate |
| TEA | Triethanolamine |
| TFA | Trifluoroacetic acid |
| THF | Tetrahydrofuran |

Abbreviations

ESMS: Electro Spray Mass Spectrometry.
HPLC: High Performance Liquid Chromatography.
LCMS: Liquid Chromatography Mass Spectrometry.
MALDI-MS: Matrix Assisted Laser Desorption Ionisation Mass Spectrometry.
Mw: Molecular weight.

Example 1

Lys$^{B29}$(N$^\epsilon$-(γ-L-glutamyl-α-D-glucamide, N$^\alpha$-(4-borono-benzoyl)) des(B30) human insulin, 9

The title compound of Example 1 was prepared by the following sequence of reactions:

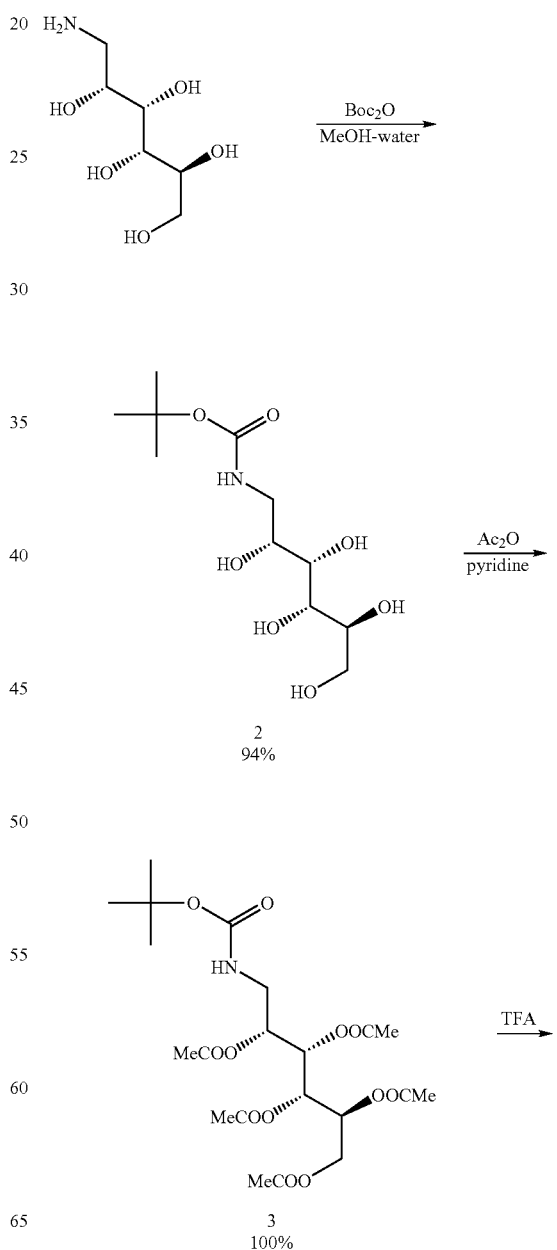

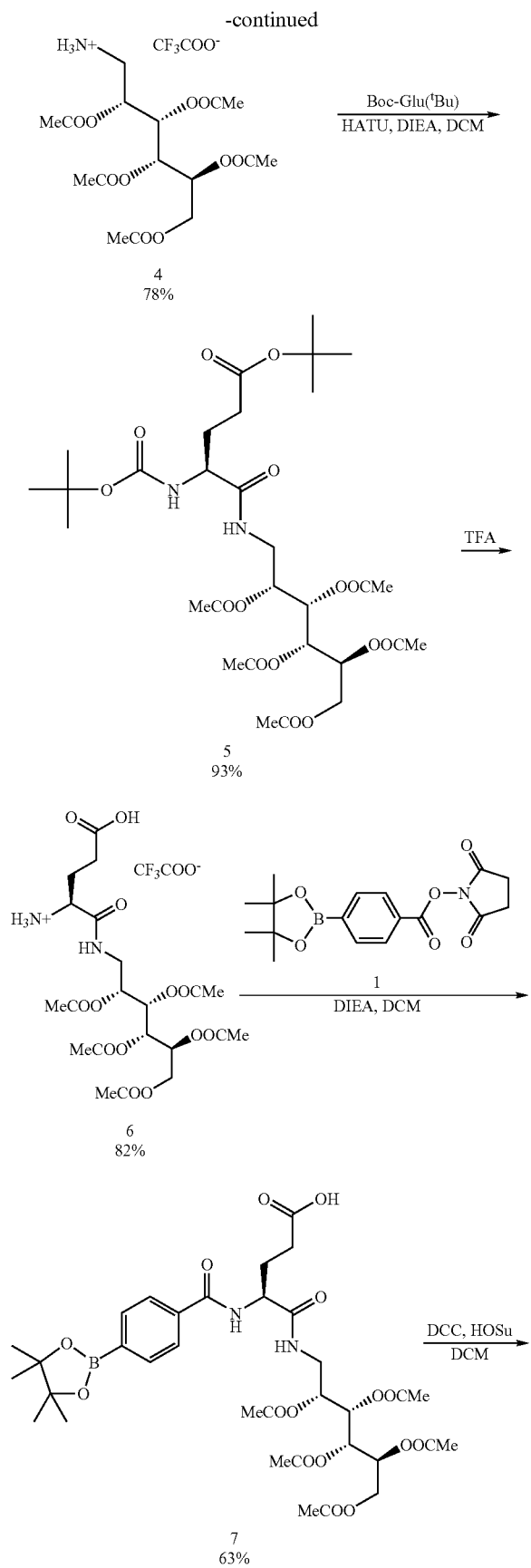
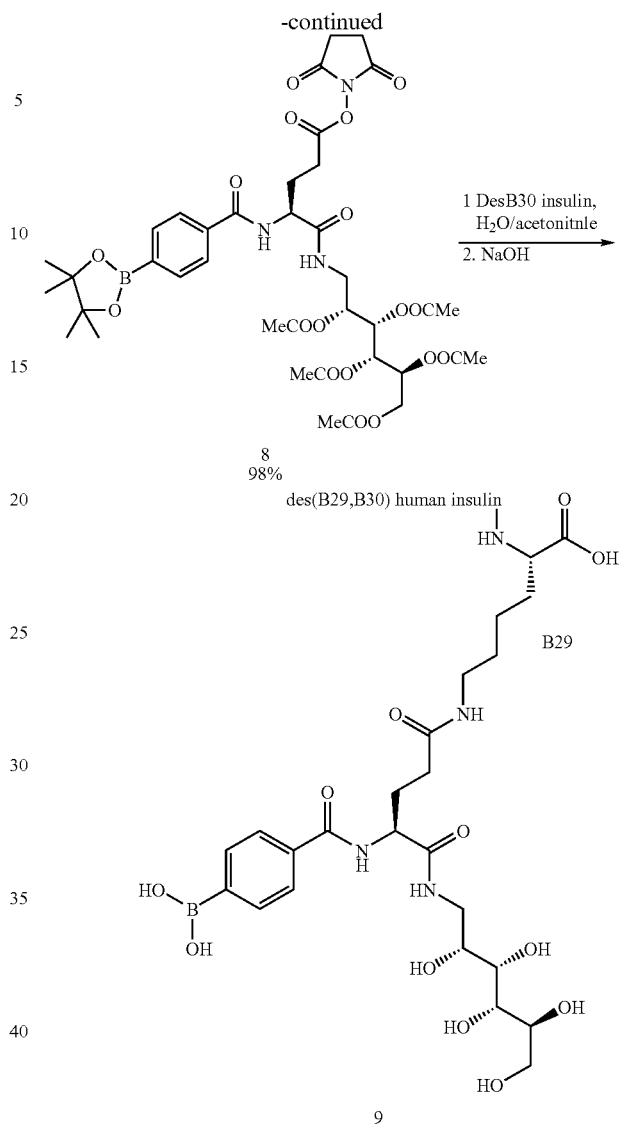

Succinimidyl 4-pinacolborono-benzoate 1 (used in step 6→7)

4-pinacolborono-benzoic acid (4.96 g, 20.0 mmol, Sigma-Aldrich) in ethyl acetate (75 ml) was cooled in an ice-bath, treated with DCC (4.33 g, 21.0 mmol) and HOSu (2.3 g, 20.0 mmol) and left at room temperature overnight. The generated dicyclohexylurea was removed by filtration, and the solvent was removed in vacuo. The active ester was recrystallized from acetone-hexane to give 1 (5.7 g, 83%).

1H-NMR (CDCl$_3$): 8.11 (d, 2H, ArH), 7.93 (d, 2H, ArH), 2.92 (s, 4H, CH$_2$CO), 1.38 (s, 12H, pinacolate).

N-Boc-D-Glucamine 2

D-Glucamine (6.67 g, 35.0 mmol, Fluka) in MeOH-water (160 ml, 1:1) was treated with Boc anhydride (10.8 g, 48.0 mmol) and the resulting suspension was stirred for 3 h. The solvent was removed in vacuo and the residue was dissolved in the minimally required amount of MeOH. Excess isopropanol was added and the solution was left in refrigerator overnight. The crystals were collected by filtration and dried in vacuo at 50° C., yielding 9.26 g (94%) of N-Boc-D-Glucamine 2, mp 81-83° C. (litt. 72-73° C., Kilonda et al. Tetrahedron 2000, 56, 1005).

1H-NMR (DMSO-$d_6$): 6.45 (bt, 1H, NH), 4.63 (d, 1H, OH), 4.24 (d, 1H, OH), 4.33 (t, 1H, OH), 4.30 (t, 1H, OH), 4.18 (d, 1H, OH), 3.55 (m, 3H, CHO), 3.45 (m, 1H, CHO), 3.38 (m, 2H, CHO), 3.10 (m, 1H, CHN), 2.91 (m, 1H, CHN), 1.36 (s, 9H, $CH_3$).

O-pentaacetyl, N-Boc-D-Glucamine 3

N-Boc-D-glucamine 2 (5.0 g, 17.5 mmol) was treated overnight at room temperature with a mixture (1:1) of acetic anhydride and pyridine (100 ml). The solvent was removed in vacuo and the residue was dissolved in ethyl acetate and washed three times with 3 M HCl, twice with 5% $NaHCO_3$, water and brine. The solution was dried ($MgSO_4$) and evaporated in vacuo to give O-pentaacetyl, N-Boc-D-glucamine, which crystallizes slowly on storage in refrigerator (quantitative).

1H-NMR ($CDCl_3$): 5.55 (m, 1H, NH), 5.36 (m, 1H, CHO), 5.06 (m, 2H, CHO), 4.77 (m, 1H, CHO), 4.26 (dd, 1H, C(6)HO), 4.13 (dd, 1H, C(6)'HO), 3.49 (dd, 1H, C(1)HN), 3.25 (dd, 1H, C(1)HN), 2.13 (s, 3H, $CH_3CO$), 2.09 (s, 6H, $2\times CH_3CO$), 2.07 (s, 3H, $CH_3CO$), 2.04 (s, 3H, $CH_3CO$), 1.44 (s, 9H, $^tBu$).

O-pentaacetyl-D-Glucamine, trifluoroacetate 4

Boc-derivative 3 (6.1 g, 12.4 mmol) was treated with TFA for 1 h, and the product 4 was precipitated by addition of cold ether, 4.87 g (78%).

1H-NMR (DMSO-$d_6$): 5.39 (m, 1H, CHO), 5.33 (m, 1H, CHO), 5.30 (m, 1H, CHO), 5.08 (m, 1H, CHO), 4.28 (dd, 1H, C(6)HO), 4.12 (dd, 1H, C(6)'HO), 3.33 (dd, 1H, C(1)HN), 3.12 (dd, 1H, C(1)HN), 2.12 (s, 6H, $2\times CH_3CO$), 2.10 (s, 3H, $CH_3CO$), 2.06 (s, 3H, $CH_3CO$), 2.05 (s, 3H, $CH_3CO$).

Boc-Glu($^tBu$)-D-glucamide(O-pentaacetyl) 5

Boc-Glu($^tBu$)-OH (1.21 g, 4.0 mmol, Bachem) in DCM (30 ml) was treated with HATU (1.52 g, 4.0 mmol) and DIEA (1.4 ml, 8.0 mmol). Glucamine-derivative 4 (2.02 g, 4.0 mmol) was dissolved in DCM (20 ml) and added drop-wise to the above mixture over 15 min. Additional DIEA was added to pH 8 (1.0 ml). The solvent was removed in vacuo and replaced with ethyl acetate, which was washed twice with 0.5 M HCl, twice with 5% $NaHCO_3$, water and brine. The solution was dried ($MgSO_4$) and evaporated in vacuo to give Boc-Glu($^tBu$)-D-glucamide(O-pentaacetyl) 5, 2.53 g (93%).

1H-NMR ($CDCl_3$): 6.64 (bd, 1H, NH), 5.48 (m, 1H, CHO), 5.30 (m, 1H, CHO), 5.13 (m, 1H, CHO), 5.05 (m, 1H, CHO), 4.26 (dd, 1H, C(6)HO), 4.11 (m, 2H, C(6)'HO+ α-CH), 3.48 (m, 2H, $CH_2N$), 2.39 (m, 1H, β-CH), 2.26 (m, 1H, b-CH'), 2.14 (s, 3H, $CH_3CO$), 2.08 (s, 9H, $3\times CH_3CO$), 2.05 (s, 3H, $CH_3CO$), 1.85 (m, 1H, γ-CH), 1.70 (m, 1H, γ-CH'), 1.45 (s, 9H, $^tBu$), 1.44 (s, 9H, $^tBu$).

Glu-D-Glucamide(pentaacetyl), trifluoroacetate 6

Glucamide-derivative 5 (2.47 g, 3.6 mmol) was treated with TFA (15 ml) at room temperature for 2.5 h. Evaporation of TFA, dissolution in DCM and dropwise addition to cold ether gives hygroscopic 6, 1.87 g (82%).

1H-NMR ($CDCl_3$): 8.24 (bt, 1H, NH), 5.44 (t, 1H, CHO), 5.33 (t, 1H, CHO), 5.18 (dd, 1H, CHO), 5.06 (m, 1H, CHO), 4.33 (dd, 1H, C(6)HO), 4.24 (t, 1H, α-CH), 4.07 (dd, 1H, C(6)'HO), 3.58 (m, 2H, $CH_2N$), 2.58 (m, 2H, β-CH), 2.13-2.04 (m, 2H, γ-$CH_2$), 2.13 (s, 3H, $CH_3CO$), 2.09 (s, 3H, $CH_3CO$), 2.08 (s, 9H, $CH_3CO$), 2.06 (s, 3H, $CH_3CO$), 2.04 (s, 3H, $CH_3CO$).

$N^\alpha$-(4-pinacolboronobenzoyl)-Glu-D-glucamide(pentaacetyl) 7

Glucamide-derivative 6 (333 mg, 0.52 mmol) was treated with active ester 1 (163 mg, 0.47 mmol) and DIEA (0.27 ml, 1.56 mmol) in DCM (3 ml) under ice cooling, and stirred at room temperature overnight. The solvent was removed in vacuo and the residue was dissolved in ethyl acetate, which was washed with 0.1 M HCl, water and brine. The solution was dried ($MgSO_4$) and evaporated to give 7, 278 mg (63%).

1H-NMR ($CDCl_3$): 7.84 (d, 2H, ArH), 7.78 (d, 2H, ArH), 7.44 (d, 1H, NH), 7.41 (t, 1H, NH), 5.47 (dd, 1H, CHO), 5.33 (dd, 1H, CHO), 5.18 (dd, 1H, CHO), 5.05 (m, 1H, CHO), 4.77 (dd, 1H, C(6)HO), 4.29 (dd, 1H, C(6)'HO), 4.11 (m, 1H, α-CH), 3.55 (m, 1H, CHN), 3.45 (m, 1H, CH'N), 2.59 (m, 1H, β-CH), 2.48 (m, 1H, β-CH'), 2.22 (m, 1H, γ-CH), 2.13 (s, 3H, $CH_3CO$), 2.06 (s, 3H, $CH_3CO$), 2.04 (s, 9H, $CH_3CO$), 2.03 (s, 3H, $CH_3CO$), 1.99 (s, 3H, $CH_3CO$), 1.36 (s, 12H, pinacolate).

$N^\alpha$-(4-pinacolboronobenzoyl)-Glu(OSu)-D-glucamide(pentaacetyl) 8

Carboxylic acid 7 (193 mg, 0.26 mmol) in DCM (3 ml) was cooled with an ice-bath and treated with DCC (54 mg, 0.26 mmol) and HOSu (30 mg, 0.26 mmol), and left at room temperature overnight. Filtration and evaporation of the solvent gives 8 (217 mg, 98%).

1H-NMR ($CDCl_3$): 7.85 (d, 2H, ArH), 7.79 (d, 2H, ArH), 7.07 (d, 1H, NH), 6.92 (t, 1H, NH), 5.46 (dd, 1H, CHO), 5.29 (dd, 1H, CHO), 5.14 (m, 1H, CHO), 5.04 (m, 1H, CHO), 4.75 (dd, 1H, C(6)HO), 4.26 (dd, 1H, C(6)'HO), 4.10 (m, 1H, α-CH), 3.51 (m, 2H, CHN), 2.81 (s, 4H, $CH_2CO$), 2.37 (m, 1H, β-CH), 2.22 (m, 1H, β-CH'), 2.14 (s, 3H, $CH_3CO$), 2.06 (s, 3H, $CH_3CO$), 2.06 (s, 9H, $CH_3CO$), 2.04 (s, 3H, $CH_3CO$), 2.00 (s, 3H, $CH_3CO$), 1.92 (m, 2H, γ-CH), 1.36 (s, 12H, pinacolate).

$Lys^{B29}(N^\epsilon$-(γ-L-glutamyl-α-D-glucamide, $N^\alpha$-(4-boronobenzoyl)) des(B30) human insulin 9

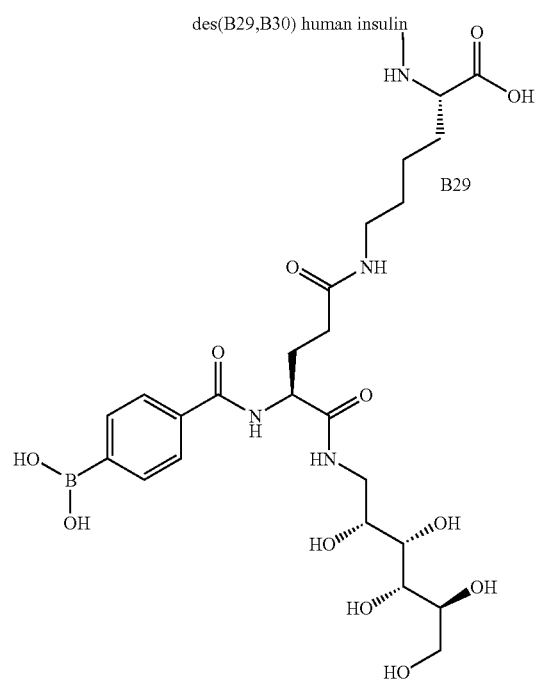

9

Des(B30) insulin (224 mg, 39 μmol) in 50 mM $Na_2CO_3$ was adjusted to pH 10.2 by drop-wise addition of 1 M NaOH. Active ester 8 (40 mg, 47 μmol) was dissolved in acetonitrile (5 ml). The solutions were mixed and the reaction was monitored by reverse-phase HPLC. The crude product was precipitated by adjustment of pH to 5.5 by use of 1 M and 0.1 M HCl, followed by cooling. The intermediary insulin O-pentaacetate was isolated by preparative reverse-phase HPLC (C-4, water/acetonitrile/0.1% TFA); and saponified by treatment with ice-cold water (0.2 ml), followed by 2 M NaOH (0.8 ml), 20 minutes. Deprotected insulin-derivative 9 was precipitated by adjustment of pH to 5.5 by drop-wise addition of 1 M HCl followed by cooling. The final product was isolated by centrifugation, washing with water and desalting on Pharmacia NAP-5 column;

LCMS 6148 ($MH^+$), 6130 ($MH^+-H_2O$), 6112 ($MH^+-2H_2O$), $C_{271}H_{401}BN_{66}O_{85}S_6$ requires 6147.

Example 2

$Lys^{B29}$-($N^\epsilon$(γ-L-glutamyl-α-D-glucamide, $N^\alpha$-(3-borono-5-nitro-benzoyl)) des(B30) human insulin 10

10 was prepared similarly to 9, starting from 3-borono-5-nitro-benzoic acid (CombiBlocks, San Diego, USA), to yield the building block 10a

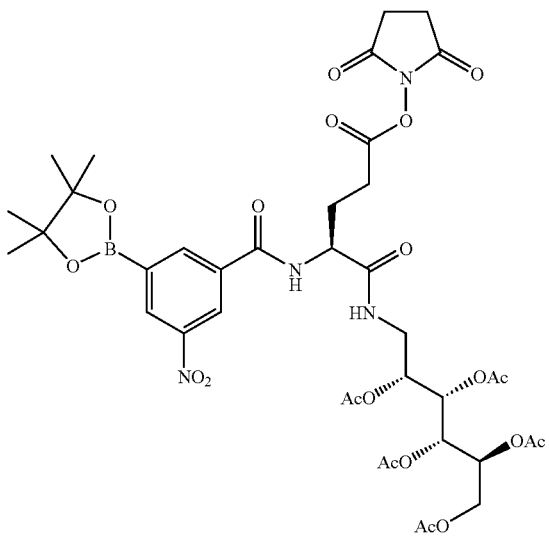

10a $^1$H NMR ($CDCl_3$): δ8.75 (s, 1H, ArH), 8.74 (s, 1H, ArH), 8.51 (s, 1H, ArH), 6.90 (t, 1H, NH), 5.46 (m, 1H, CHO), 5.29 (m, 1H, CHO), 5.13 (1H, CHO), 5.05 (m, 1H, CHO), 4.79 (s, 1H, αH), 4.29 (dd, 1H, C(6)HO), 4.10 (dd, 1H, C(6)'HO), 3.52 (m, 2H, $CH_2N$), 2.90 (m, 1H, γH), 2.86 (s, 4H, $CH_2CH_2$), 2.77 (m, 1H, γH'), 2.39 (m, 1H, βH), 2.28 (m, 1H, βH'), 2.14 (s, 3H, $CH_3CO$), 2.08 (s, 3H, $CH_3CO$), 2.06 (s, 6H, 2×$CH_3CO$), 2.03 (s, 3H, $CH_3CO$), 1.37 (s, 12H, pinacol).

The intermediary insulin O-pentaacetate was isolated by preparative reverse-phase HPLC (C-4, water/acetonitrile/0.1% TFA) and saponified by treatment with ice-cold water (0.2 ml), followed by 2 M NaOH (0.8 ml) for 20 minutes. Deprotected insulin-derivative 10 was precipitated by adjustment of pH to 5.5 by drop-wise addition of 1 M HCl followed by cooling. The final product was isolated by centrifugation, washing with water and desalting on Pharmacia NAP-5 column;

LCMS 6193 ($MH^+$), 6175 ($MH^+-H_2O$), 6157 ($MH^+-2H_2O$), $C_{271}H_{400}BN_{67}O_{87}S_6$ requires 6192.

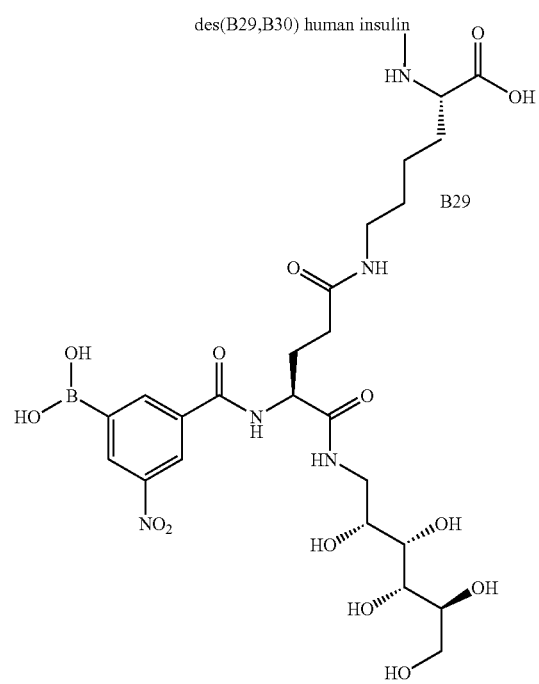

10

Example 3

$Lys^{B29}$($N^\epsilon$-(γ-L-glutamyl-α-(tris(hydroxymethyl)methylamide), $N^\alpha$-(4-borono-benzoyl)) des(B30) human insulin 12

12 was prepared similarly to 9, starting from tris(acetyloxymethyl)aminomethane hydrochloride 11.

Tris(acetyloxymethyl)aminomethane hydrochloride 11

Tris(hydroxymethyl)aminomethane hydrochloride (100 g, 0.64 mol) in a mixture of acetic anhydride (222 ml, 2.35 mol) and acetic acid (305 ml, 5.3 mol) was heated at 100° C. overnight. The solvent was removed in vacuo and the residue was washed three times with ether. A portion of the material was recrystallized from ethanol-ether to give 11, 41 g (23%).

1H-NMR ($CDCl_3$): 9.11 (bs, 3H, NH), 4.39 (s, 6H, $CH_2O$), 2.18 (s, 9H, $CH_3CO$).

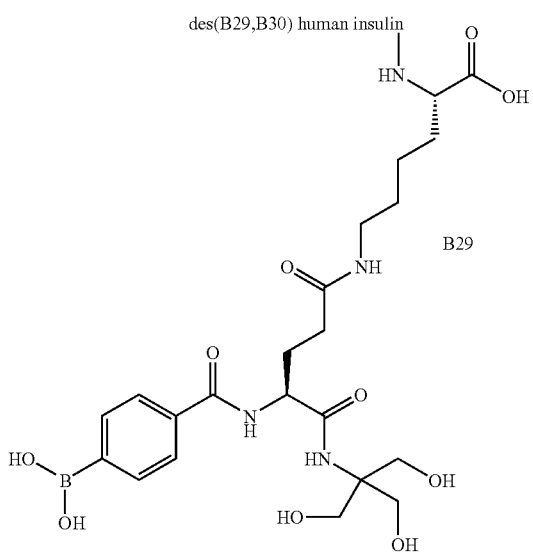

Insulin derivative 12 was isolated by preparative reverse-phase HPLC (C-4, water/acetonitrile/0.1% TFA), followed by saponification and desalting as described above;

LCMS 6088 (MH$^+$), 6070 (MH$^+$–H$_2$O), 6052 (MH$^+$–2H$_2$O), C$_{269}$H$_{397}$BN$_{66}$O$_{83}$S$_6$ requires 6087.

Example 4

Lys$^{B29}$(N$^\epsilon$-(γ-L-glutamyl-α-(tris(hydroxymethyl) methylamide), N$^\alpha$-(3-borono-5-nitro-benzoyl)) des(B30) human insulin, 13

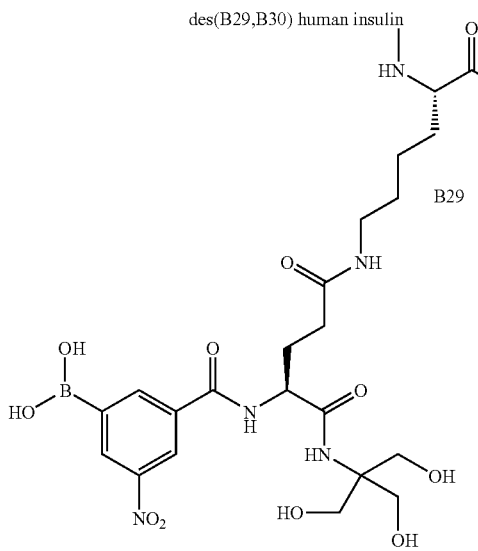

13 was prepared similarly to 9, starting from tris-derivative 11.

Insulin derivative 13 was isolated by preparative reverse-phase HPLC (C-4, water/acetonitrile/0.1% TFA), followed by saponification and desalting as described above;

LCMS 6133 (MH$^+$), 6115 (MH$^+$–H$_2$O), 6097 (MH$^+$–2H$_2$O), C$_{269}$H$_{396}$BN$_{67}$O$_{85}$S$_6$ requires 6132.

Example 5

Lys$^{B29}$(N$^\epsilon$-(acetyliminoacet-N-methyl-glucamide), N-(4-borono-phenylsulfonyl)) des(B30) human insulin 14

Lithium 4-sulfinyl-phenylboronic acid N-methyl-diethanolamine ester 15

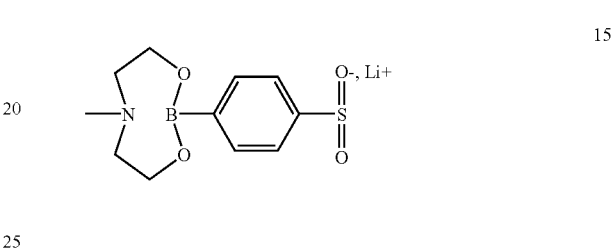

To a stirred solution of 4-bromobenzeneboronic acid N-methyldiethanolamine ester (6.62 g, 23.4 mmol) in THF (200 mL) was added drop-wise 1.43 M solution in hexanes n-BuLi (14.8 mL, 21.0 mmol) over a 5-min period at –105° C. The mixture was stirred at –105° C. for 15 min. Gaseous sulphur dioxide (ca. 7 g) was added causing an immediate precipitation and a ca 40° C. increase in the internal temperature. The mixture was allowed to warm to room temperature and stirred for 1 h. The precipitated lithium sulfinate was isolated by filtration under N$_2$ (g), washed with THF (100 mL) and dried in vacuo providing 5.74 g (99%) of the title compound as a solid.

1H-NMR (DMSO-d$_6$): δ7.43 (d, 2H), 7.35 (d, 2H), 3.97-3.83 (m, 4H), 3.26-3.19 (m, 2H), 2.98-2.89 (m, 2H), 2.17 (s, 3H).

Lithium 3-sulfinyl-phenylboronic acid N-methyl-diethanolamine ester 16

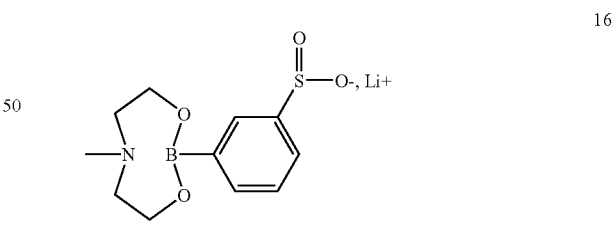

To a stirred solution of 3-bromobenzeneboronic acid N-methyldiethanolamine ester (3.31 g, 11.7 mmol) in THF (100 mL) was added drop-wise 1.43 M solution in hexanes n-BuLi (7.4 mL, 10.5 mmol) over a 3-min period at –78° C. The mixture was stirred at –78° C. for 15 min. Gaseous sulphur dioxide (ca. 5 g) was added causing an immediate precipitation and a ca 40° C. increase in the internal temperature. The mixture was allowed to warm to room temperature and stirred for 1 h. The precipitated lithium sulfinate was isolated by filtration under N₂ (g), washed with THF (50 mL) and dried in vacuo providing 2.81 g (97%) of the title compound as a solid.

1H-NMR (DMSO-d₆): δ7.66 (s, 1H), 7.39-7.32 (m, 2H), 7.17 (t, 1H), 3.97-3.84 (m, 4H), 3.27-3.21 (m, 2H), 2.97-2.89 (m, 2H), 2.18 (s, 3H).

N-Boc-iminodiacetic anhydride 17

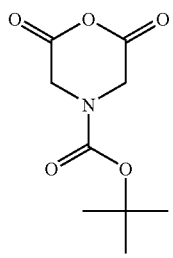

Iminodiacetic acid (5.0 g, 37.6 mmol) in THF-water (1:1, 100 ml) was treated with Na—HCO₃ (12.6 g, 150 mmol) portion-wise over 15 minutes. Boc anhydride (9.85, 45.1 mmol) was added and the mixture was stirred at room temperature for 2 days. THF was removed by evaporation in vacuo and the aqueous solution was washed with ether (2×), acidified using conc. HCl to pH 1 under cooling with ice bath and extracted with AcOEt (3×). The organic phase was washed with brine, dried (Na₂SO₄) and evaporated in vacuo to yield 2.55 g (29%). Crude N-Boc-iminodiacetic acid (2.0 g, 8.6 mmol) was dissolved in AcOEt (100 ml), cooled to 0° C., and treated with triethylamine (2.43 ml, 17.4 mmol) and powdered triphosgene (0.84 g, 2.83 mmol). The suspension was stirred 15 minutes under cooling, and 15 minutes at room temperature. The solution was washed with brine, dried (MgSO₄) and evaporated in vacuo to yield 17, 1.53 g (83%).

1H-NMR (CDCl₃): δ4.42 (s, 4H, CH₂N), 1.49 (s, 9H, Buᵗ).

N-methyl-D-Glucamine O-pentaacetate trifluoroacetate 18

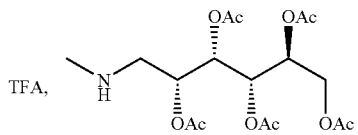

Compound 18 was prepared analogously to O-pentaacetyl-D-Glucamine, trifluoroacetate 4.

1H-NMR (CDCl₃): δ 5.40 (m, 1H, CHO), 5.37 (m, 1H, CHO), 5.33 (m, 1H, CHO), 5.08 (m, 1H, CHO), 4.26 (dd, 1H, C(6)HO), 4.13 (dd, 1H, C(6)'HO), 3.29 (dd, 1H, C(1)HN), 3.20 (dd, 1H, C(1)HN), 2.71 (s, 3H, NMe), 2.14 (s, 3H, CH₃CO), 2.09 (s, 3H, CH₃CO), 2.08 (s, 3H, CH₃CO), 2.06 (s, 3H, CH₃CO), 2.04 (s, 3H, CH₃CO).

Iminoacetic acid, N-acet-(O-pentaacetate-N-methyl-D-Glucamide), trifluoroacetate 19

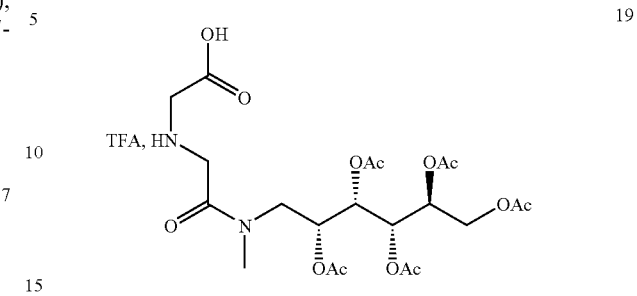

Anhydride 17 (1.53 g, 7.1 mmol) in DCM (30 ml) was treated with DIEA (1.22 ml, 14.2 mmol) followed by amine salt 18 (4.06 g, 7.8 mmol) in DCM (40 ml), which was added dropwise over 5 minutes. The mixture was stirred overnight and the solvent was evaporated in vacuo. The residue was dissolved in AcOEt, washed with 0.5 M HCl and water (3×), brine, dried (MgSO₄) and evaporated in vacuo to yield 3.59 g (81%). The crude product was cooled with ice and treated with TFA (20 ml) for 2 hours. The solvent was evaporated, and the residue was dissolved in CHCl₃ and added to cold ether. The precipitate was collected by filtration and dried to yield 19, 2.94 g (82%).

1H-NMR (CDCl₃): δ7.86 (bs, 2H, NH), 5.39 (m, 1H, CHO), 5.33 (m, 1H, CHO), 5.30 (m, 1H, CHO), 5.02 (m, 1H, CHO), 4.33 (dd, 1H, C(6)HO), 4.09 (s, 2H, CH₂N), 4.08 (dd, 1H, C(6)'HO), 3.98 (s, 2H, CH₂N), 3.72 (dd, 1H, C(1)HN), 3.40 (dd, 1H, C(1)HN), 2.97 (s, 3H, NMe), 2.12 (s, 3H, CH₃CO), 2.09 (s, 3H, CH₃CO), 2.07 (s, 3H, CH₃CO), 2.06 (s, 3H, CH₃CO), 2.04 (s, 3H, CH₃CO).

Succinimidyl N-(4-pinacolboronophenylsulfonyl)-iminodiacetate, O-pentaacetyl-N-methyl-D-glucamide 20

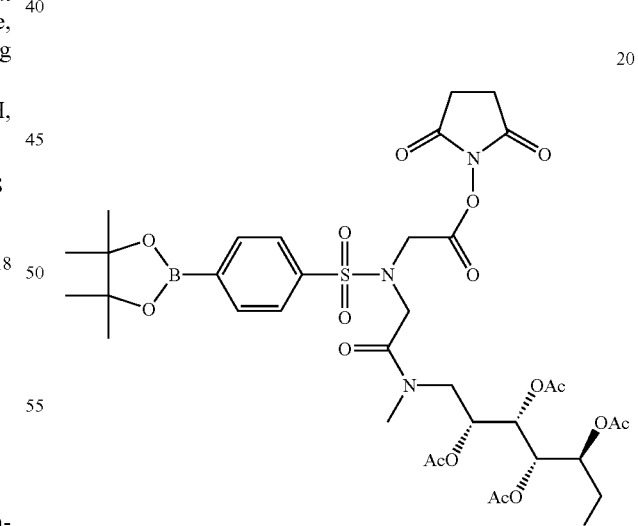

Sulfinate 15 330 mg, 1.2 mmol) in DCM (10 ml) was treated with N-chloro-succinimide (160 mg, 1.2 mmol) and the mixture was stirred for 1 hour. DIEA (544 μl, 3.2 mmol) was added, followed by amine salt 19 (840 mg, 1.32 mmol) in DCM (10 ml). The mixture was stirred overnight, and the solvent evaporated and the residue treated with AcOEt, followed by 0.1 M HCl to pH 2. The mixture was stirred 10 minutes and washed with water (2×). Pinacol (154 mg, 1.3 mmol) and $MgSO_4$ were added. After 30 minutes, the mixture was washed with water (2×) and brine, dried ($MgSO_4$) and evaporated in vacuo, to yield the acid, 551 mg (57%). The crude product was dissolved in MeCN (5 ml), cooled with an ice bath and treated with HOSu (79 mg, 0.68 mmol) and DCC (141 mg, 0.68 mmol). The mixture was stirred at RT overnight, filtered and evaporated in vacuo to yield 20, 500 mg (93%).

$^1$H NMR ($CDCl_3$): δ7.91 (d, 2H, ArH), 7.83 (d, 1H, ArH), 5.40 (m, 1H, CHO), 5.28 (m, 2H, 2×CHO), 5.01 (m, 1H, CHO), 4.58 (s, 2H, $CH_2N$), 4.28 (dd, 1H, C(6)HO), 4.22 (s, 2H, $CH_2N$), 4.07 (dd, 1H, C(6)'HO), 3.59 (dd, 1H, C(1)HN), 3.43 (dd, 1H, C(1)HN), 2.97 (s, 3H, NMe), 2.80 (s, 4H, $CH_2CH_2$), 2.07 (s, 3H, $CH_3CO$), 2.06 (s, 3H, $CH_3CO$), 2.05 (s, 3H, $CH_3CO$), 2.04 (s, 3H, $CH_3CO$), 2.03 (s, 3H, $CH_3CO$), 1.35 (s, 12H, pinacol).

$Lys^{B29}$($N^\epsilon$-(acetyliminoacet-N-methyl-D-glucamide), N-(4-borono-phenylsulfonyl)) des(B30) human insulin 14

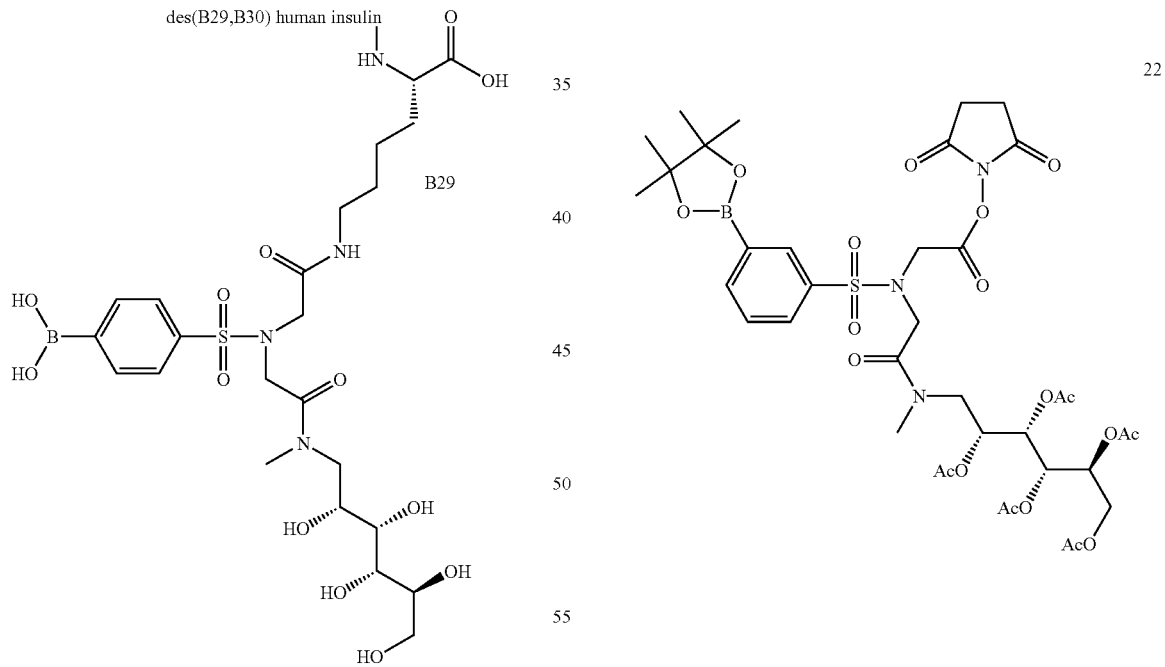

Des(B30) human insulin (200 mg, 35 μmol) was dissolved in 100 mM $Na_2CO_3$ (2.5 ml), pH 10.5. Active ester 20 (37 mg, 42 μmol) was dissolved in acetonitrile (2.5 ml). The solutions were mixed and the reaction was monitored by reverse-phase HPLC. The crude product was precipitated by adjustment of pH to 5.5 by use of 1 M HCl, followed by cooling with ice bath. The intermediary O-pentaacetate insulin was isolated by preparative reverse-phase HPLC (C-4, water/acetonitrile/0.1% TFA);

LCMS 6380 ($MH^+$), 6372 ($MH^+-H_2O$), 6354 ($MH^+-2H_2O$), $C_{279}H_{409}BN_{66}O_{91}S_7$ requires 6379. The O-acetyl groups were saponified by treatment with ice-cold water (2 ml), followed by 0.2 M NaOH (8 ml), for 20 minutes on ice bath. The crude product was precipitated by adjustment of pH to 5.5 by drop-wise addition of 1 M HCl followed by cooling, centrifugation and 3× washing with water. Insulin derivative 14 was isolated upon desalting on Pharmacia NAP-5 column;

LCMS 6184 ($MH^+$), 6166 ($MH^+-H_2O$), 6148 ($MH^+-2H_2O$), $C_{270}H_{401}BN_{66}O_{86}S_7$ requires 6183.

Example 6

$Lys^{B29}$($N^\epsilon$-(acetyliminoacet-N-methyl-glucamide), N-(3-borono-phenylsulfonyl)) des(B30) human insulin 21

Succinimidyl N-(3-pinacolboronophenylsulfonyl)-iminodiacetate, O-pentaacetyl-N-methyl-D-glucamide 22

Active ester 22 was prepared analogously to 20 from sulfinate 16.

1H-NMR ($CDCl_3$) δ 8.25 (s, 1H, ArH), 7.97 (d, 1H, ArH), 7.92 (d, 1H, ArH), 7.50 (t, 1H, ArH), 5.39 (m, 1H, CHO), 5.29 (m, 2H, 2×CHO), 5.02 (m, 1H, CHO), 4.60 (s, 2H, $CH_2N$), 4.29 (dd, 1H, C(6)HO), 4.24 (s, 2H, $CH_2N$), 4.08 (dd, 1H, C(6)'HO), 3.59 (dd, 1H, C(1)HN), 3.43 (dd, 1H, C(1)HN), 3.00 (s, 3H, NMe), 2.80 (s, 4H, $CH_2CH_2$), 2.07 (s, 3H, $CH_3CO$), 2.06 (s, 6H, 2×$CH_3CO$), 2.03 (s, 3H, $CH_3CO$), 2.00 (s, 3H, $CH_3CO$), 1.36 (s, 12H, pinacol).

Lys$^{B29}$(N$^\epsilon$-(acetyliminoacet-N-methyl-glucamide), N-(3-borono-phenylsulfonyl)) des(B30) human insulin 21

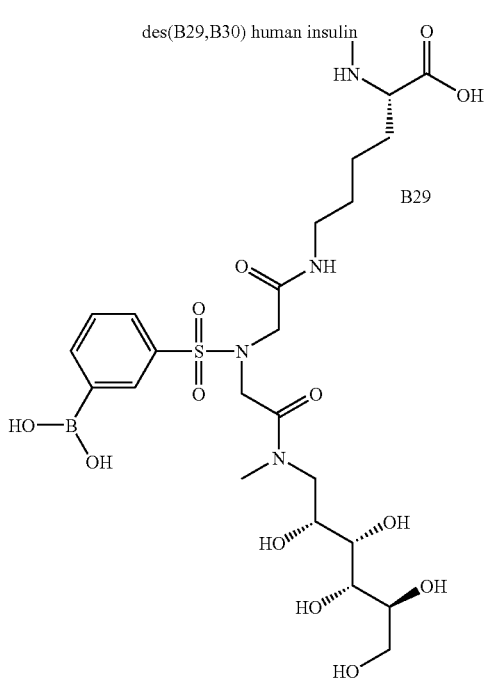

Prepared analogously to 14 from active ester 22;
LCMS 6184 (MH$^+$), 6166 (MH$^+$–H$_2$O), 6148 (MH$^+$–2H$_2$O), C$_{270}$H$_{401}$BN$_{66}$O$_{86}$S$_7$ requires 6183.

Example 7

Lys$^{B29}$(N$^\epsilon$-(4-carboxyphenylalanine-N-methyl-glucamide), N$^\alpha$-(4-borono-phenylsulfonyl)) des(B30), human insulin 23

N-Boc-phenylalanine-4-(tert-butyl-carboxylate), O-pentaacetyl-N-methyl-D-glucamide 24

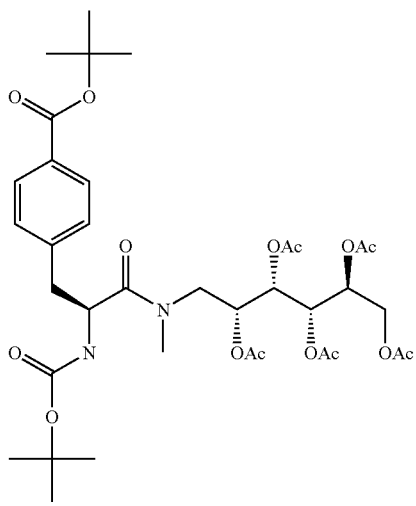

N-Boc-(4-tert-butoxycarbonylphenyl)alanine dicyclohexylamine salt (from Bachem, Bubendorf, Switzerland), (1.0 g, 1.83 mmol) in DCM (15 ml) was treated with TBTU (0.88 g, 2.74 mmol) and DIEA (1.41 ml, 5.5 mmol). Glucamine-derivative 18 (1.56 g, 3.0 mmol) in DCM (15 ml) was added, and the mixture was stirred overnight. The solvent was removed in vacuo, and the residue was dissolved in AcOEt, and washed with 0.1 M HCl (2×), 5% NaHCO$_3$ (2×), water and brine, then dried (MgSO$_4$) and evaporated to yield 24, 1.43 g (100%).

$^1$H NMR (CDCl$_3$): δ7.89 (d, 2H, ArH), 7.24 (d, 2H, ArH), 5.47 (dd, 1H, CHO), 5.27 (m, 2H, 2×CHO), 5.04 (m, 1H, CHO), 4.79 (m, 1H, αH), 4.29 (dd, 1H, C(6)HO), 4.10 (dd, 1H, C(6)HO), 3.56 (m, 2H, CH$_2$N), 3.02 (m, 1H, βH), 2.97 (m, 1H, βH'), 2.85 (s, 3H, NMe), 2.14 (s, 3H, CH$_3$CO), 2.08 (s, 6H, CH$_3$CO), 2.07(s, 3H, CH$_3$CO), 2.04 (s, 3H, CH$_3$CO), 2.02 (s, 3H, CH$_3$CO), 1.58 (s, 9H, Bu$^t$), 1.38 (s, 9H, Bu$^t$).

Phenylalanine-4-carboxylic acid, O-pentaacetyl-N-methyl-D-glucamide, trifluoroacetate 25

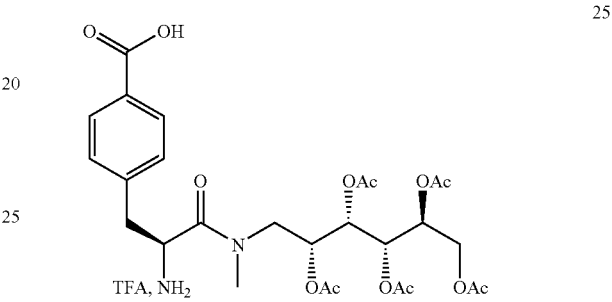

Boc-protected 24 (1.35 g, 1.80 mmol) was dissolved in TFA (12 ml) and left for 2 hours. The solvent was evaporated and the residue dissolved in CHCl$_3$ and precipitated from cold diethyl ether to yield 25, 0.82 g (64%).

$^1$H NMR (CDCl$_3$): δ7.78 (d, 2H, ArH), 7.34 (d, 2H, ArH), 5.42 (dd, 1H, CHO), 5.37 (m, 1H, CHO), 5.31 (m, 1H, CHO), 5.06 (m, 1H, CHO), 4.73 (m, 1H, αH), 4.29 (dd, 1H, C(6)HO), 4.06 (m, 3H, C(6)HO+CH$_2$N), 3.25 (m, 1H, βH), 3.14 (m, 1H, βH'), 3.11 (s, 3H, NMe), 2.16 (s, 3H, CH$_3$CO), 2.10 (s, 3H, CH$_3$CO), 2.09 (s, 3H, CH$_3$CO), 2.07 (s, 3H, CH$_3$CO), 2.06 (s, 3H, CH$_3$CO).

Succinimidyl N-(4-pinacolboronophenylsulfonyl)-phenylalanine-4-carboxylate, O-pentaacetyl-N-methyl-D-glucamide 26

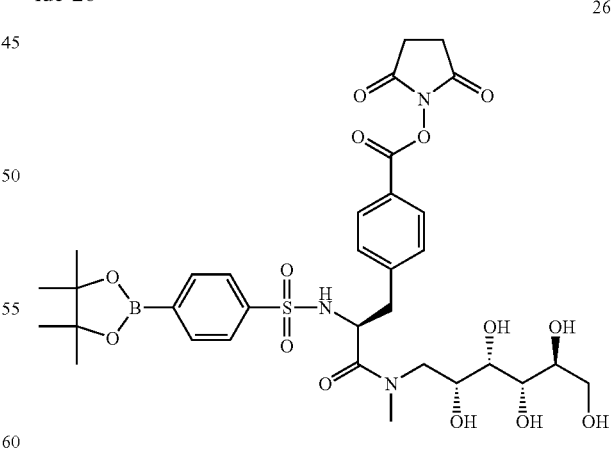

Sulfinate 15 (70 mg, 0.26 mmol) in THF (6 ml) was treated with N-chloro-succinimide (34 mg, 0.26 mmol) and the mixture was stirred for 1 hour. DIEA (132 μl, 0.78 mmol) was added, followed by compound 25 (200 mg, 0.28 mmol) in DCM (2 ml). The mixture was stirred overnight, the solvent was evaporated, and the residue treated with AcOEt, followed by 0.1 M HCl to pH 2. The mixture was stirred 10 minutes and washed with water (2×). Pinacol (36 mg, 0.30 mmol) and MgSO$_4$ were added. After 30 minutes, the mixture was washed with water (2×) and brine, dried (MgSO$_4$) and evaporated in vacuo, to yield 104 mg (47%). The crude carboxylic acid was dissolved in MeCN (2 ml), ice-cooled and treated with HOSu (14 mg, 0.12 mmol) and DCC (24 mg, 0.12 mmol). The mixture was stirred overnight, filtered and evaporated in vacuo to give 106 mg (92%).

$^1$H NMR (CDCl$_3$): δ8.01 (d, 2H, ArH), 7.89 (d, 2H, ArH), 7.75 (d, 2H, ArH), 7.28 (d, 2H, ArH), 5.70 (d, 1H, NH), 5.37 (dd, 1H, CHO), 5.22 (m, 1H, CHO), 5.19 (m, 1H, CHO), 5.02 (m, 1H, CHO), 4.37 (m, 1H, αH), 4.28 (dd, 1H, C(6)HO), 4.08 (m, 1H, C(6)HO), 3.50 (m, 1H, CH$_2$N), 3.00 (m, 2H, βH$_2$), 2.89 (s, 4H, CH$_2$CH$_2$), 2.79 (s, 3H, NMe), 2.12 (s, 3H, CH$_3$CO), 2.07 (s, 6H, 2×CH$_3$CO), 2.03 (s, 3H, CH$_3$CO), 2.00 (s, 3H, CH$_3$CO), 1.36 (s, 12H, pinacol).

Lys$^{B29}$(N$^\epsilon$-(4-carboxyphenylalanine-N-methyl-glucamide), N$^\alpha$-(3-borono-phenylsulfonyl)) des(B30), human insulin 23

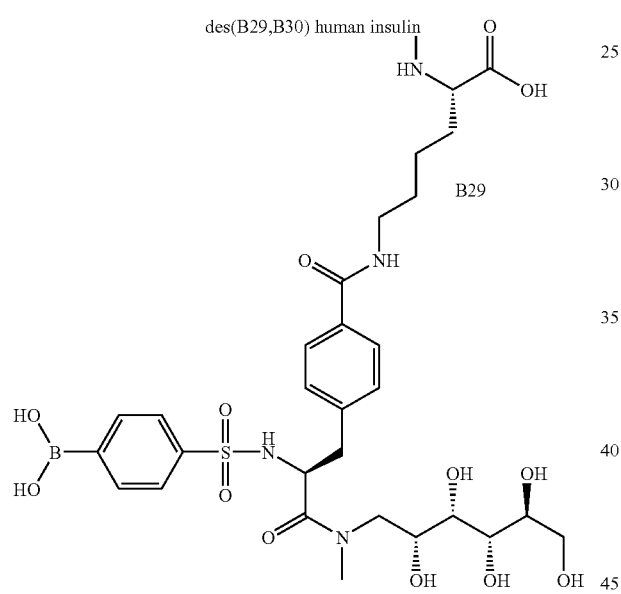

Des(B30) human insulin (262 mg, 46 μmol) was dissolved in 100 mM Na$_2$CO$_3$ (2.9 ml), pH 10.5. Active ester 26 (53 mg, 55 μmol) was dissolved in acetonitrile (2.9 ml). The solutions were mixed and the reaction was monitored by reverse-phase HPLC. The crude product was precipitated by adjustment of pH to 5.5 by use of 1 M HCl, followed by cooling. The intermediary O-pentaacetate insulin was isolated by preparative ing. The intermediary O-pentaacetate insulin was isolated by preparative reverse-phase HPLC (C-4, water/acetonitrile/0.1% TFA);

LCMS 6456 (MH$^+$), 6438 (MH$^+$–H$_2$O), 6420 (MH$^+$–2H$_2$O), C$_{285}$H$_{413}$BN$_{66}$O$_{91}$S$_7$ requires 6455.

The O-acetyl groups were saponified by treatment with ice-cold water (2 ml), followed by 0.2 M NaOH (10 ml), for 20 minutes on ice bath. The crude product was precipitated by adjustment of pH to 5.5 by drop-wise addition of 1 M HCl followed by cooling, centrifugation and washing with water (3×). Insulin derivative 23 was isolated upon desalting on Pharmacia NAP-5;

LCMS 6260 (MH$^+$), 6242 (MH$^+$–H$_2$O), 6224 (MH$^+$–2H$_2$O), C$_{276}$H$_{405}$BN$_{66}$O$_{86}$S$_7$ requires 6259.

Example 8

Lys$^{B29}$(N$^\epsilon$-(acetyliminoacet-N-methyl-glucamide), N-(3-borono-phenylsulfonyl)) des(B30) human insulin 27

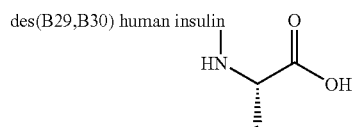
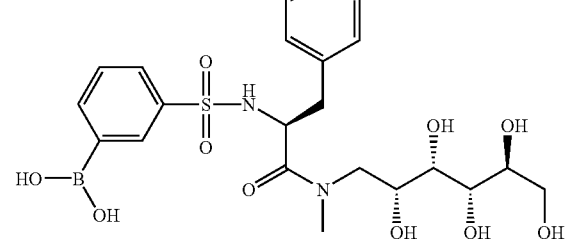

Prepared analogously to 23 from sulfinate 16.

LCMS 6260 (MH$^+$), 6242 (MH$^+$–H$_2$O), 6224 (MH$^+$–2H$_2$O), C$_{276}$H$_{405}$BN$_{66}$O$_{86}$S$_7$ requires 6259.

Example 9

Lys$^{B29}$(N$^\epsilon$-(γ-L-glutamyl-α-D-glucamide, N$^\alpha$-(3-borono-5-nitro-benzoyl)), B13Gln, human insulin 28

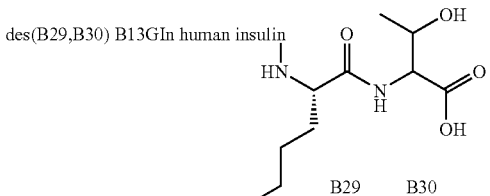
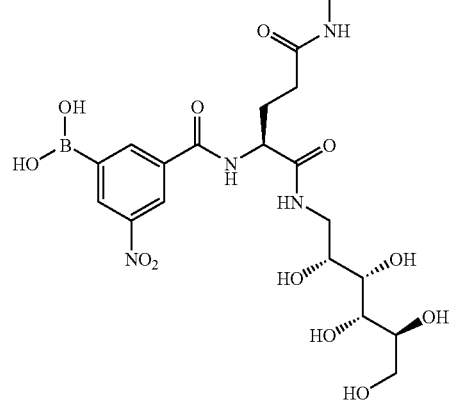

Insulin 28 was prepared similarly to 23, starting from B13Gln human insulin;

LCMS 6293 (MH$^+$), 6275 (MH$^+$–H$_2$O), 6224 (MH$^+$–2H$_2$O), C$_{275}$H$_{408}$BN$_{69}$O$_{88}$S$_6$ requires 6292

Example 10

Lys$^{B29}$(N$^\epsilon$-(4-borono-phenylsulfonyl) des(B30) human insulin 29

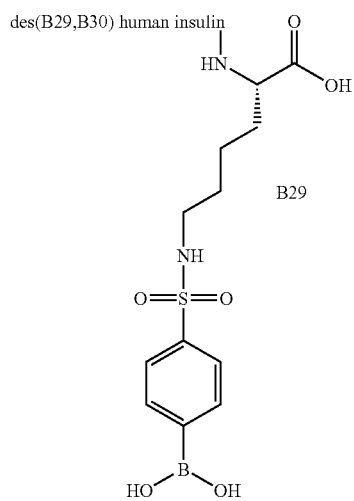

Des(B30) human insulin (75 mg, 13 µmol) was dissolved DMSO (1.5 ml) by gentle shaking for 1 hour.

TEA (18 µl, 131 µmol) was added, followed by lithium sulfinate 15 (4 mg, 13 µmol). The reaction was monitored by reverse-phase HPLC. The crude product was precipitated upon dilution with water and adjustment of pH to 5.5 by use of 1 M HCl, followed by cooling. The insulin sulfonylated insulin was isolated by preparative reverse-phase HPLC (C-4, water/acetonitrile/0.1% TFA);

LCMS 5892 (MH$^+$), 5874 (MH$^+$–H$_2$O), 5856 (MH$^+$–2H$_2$O), C$_{259}$H$_{381}$BN$_{64}$O$_{79}$S$_7$ requires 5891.

The invention claimed is:

1. An insulin derivative comprising a glucose-sensing group and a polyol moiety, wherein the glucose-sensing group is an aryl boronate group and is attached to the insulin moiety via a first linker, the first linker being selected from the group consisting of γ-glutamyl, α-glutamyl, β-aspartyl, α-aspartyl, β-alanine, 4-carboxy-phenylalanine, iminodiacetic acid, piperazine, and aniline, wherein the aryl boronate group is selected from the group consisting of A-Z and AA-AE below, wherein the substituent R in each of the groups designates the insulin moiety of the molecule including a polyol substituent and the first linker, wherein the polyol substituent is attached to the insulin moiety via the first linker, R' designates a substituent selected among the options hydrogen, methyl, ethyl, propyl, isopropyl and benzyl and R'' designates a substituent selected among the options D-glucamine, L-glucamine, N-methyl-glucamine, galactamine, N-methyl-galactamine, mannamine, N-methyl-mannamine and tris(hydroxymethyl)aminomethane

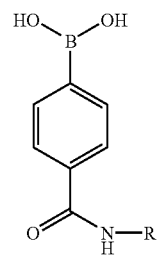

A

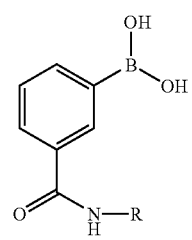

B

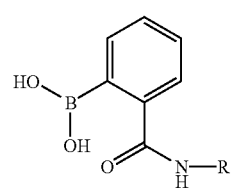

C

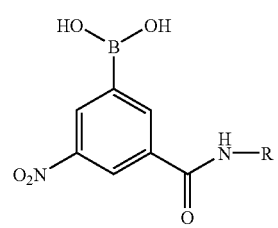

D

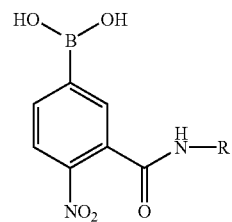

E

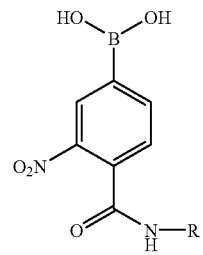

F

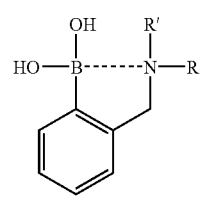

G

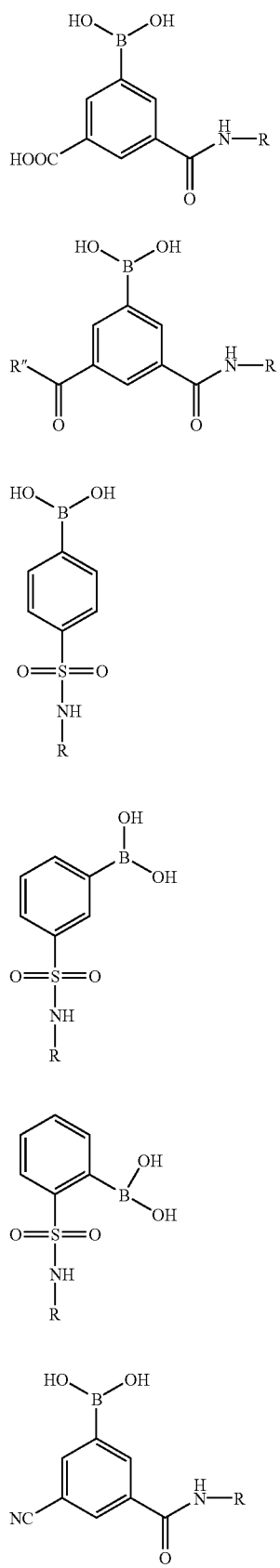
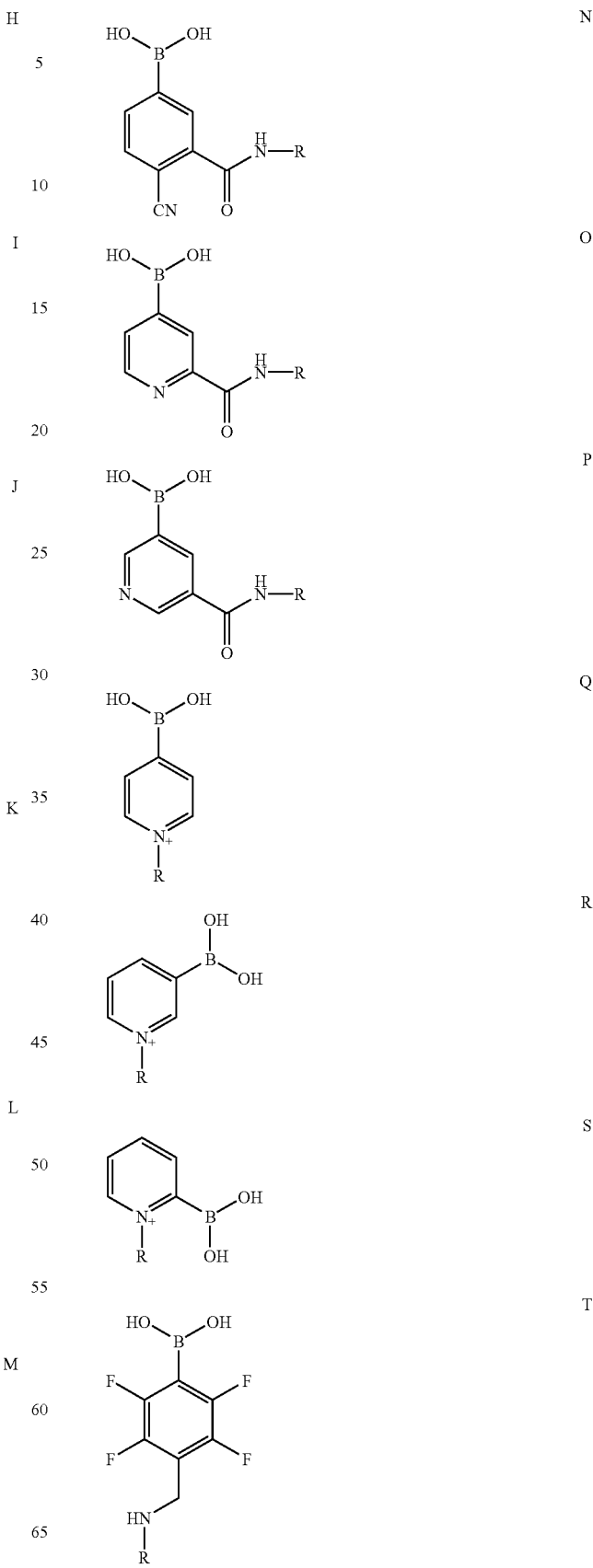

-continued

U

V

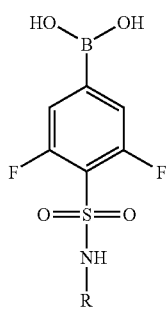
Y

X

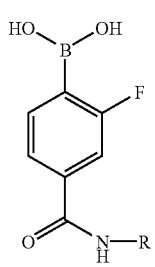
Z

-continued

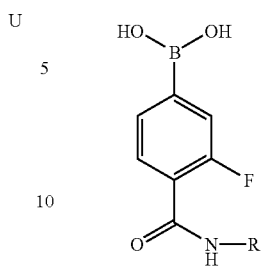
AA

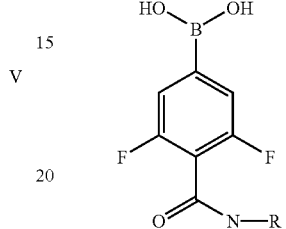
AB

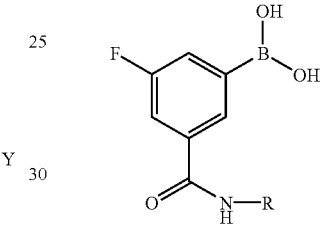
AC

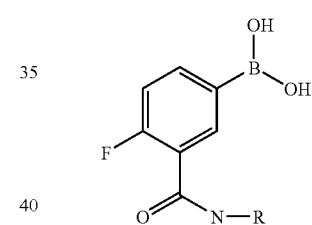
AD

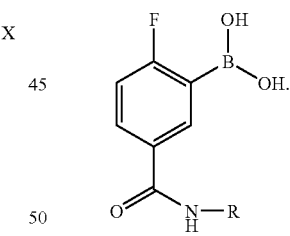
AE

2. An insulin derivative according to claim 1, wherein said derivative is derived from natural insulin.

3. An insulin derivative according to claim 1, wherein said derivative is derived from an insulin analogue.

4. An insulin derivative according to claim 1, wherein said derivative has an affinity for glucose between about 0.01 μM to 10 mM.

5. An insulin derivative according to claim 1, wherein the aryl boronate group has an electron-withdrawing substituent.

6. An insulin derivative according to claim 5, wherein the electron-withdrawing substituent is selected from the group consisting of sulfonyl, carboxy, nitro, cyano and fluoro.

7. An insulin derivative according to claim 5, wherein said boronate group has an amino group in proximity in the form of a 2-aminomethylarylboronate.

8. An insulin derivative according to claim 7, wherein said amino group is within about 2.0 Ångstrom from the boron atom.

9. An insulin derivative according to claim 1, wherein the arylboronate group is attached to the insulin moiety via the first linker through the α-amino group of the N-terminal amino acid residue of the insulin A chain or the B chain or via the ε-amino group of a Lys residue at position B3, B28, B29 or B30 or a Orn residue, a Dap residue, a Dab residue, an Asp residue or a Glu residue at position B30.

10. An insulin derivative according to claim 1, wherein the glucose sensing aryl boronate is a part of the amino acid residue in position B26 of the insulin moiety.

11. An insulin derivative according to claim 1, wherein the aryl boronate group is part of a substituent capable of effecting the formation of high-molecular-weight aggregates.

12. An insulin derivative according to claim 11, wherein the aryl boronate causes aggregation by binding to a polyol moiety.

13. An insulin derivative according to claim 12, wherein the polyol moiety is a derivative of D- or L-forms of glucamine, N-methyl-glucamine, galactamine, N-methyl-galactamine, mannamine, N-methyl-mannamine, gluconic acid, sorbitol, galactol, mannitol, quinic acid, shikimic acid, inositol, pinitol, tris(hydroxymethyl)-aminomethane, pentaerythritol and their derivatives, or derivatives of glucose, fructose, galactose, mannose or other carbohydrates.

14. An insulin derivative according to claim 13, wherein the polyol moiety is attached to the insulin moiety via the α-amino group of the N-terminal amino acid residue of the A chain or the B chain or via the ε-amino group of a Lys residue at position B3, B28, B29 or B30 or a Orn residue, a Dap residue, a Dab residue, an Asp residue or a Glu residue at position B30.

15. An insulin derivative according to claim 13, wherein the polyol moiety is attached to the insulin moiety via the first linker or via a second linker.

16. An insulin derivative according to claim 15, wherein the second linker is selected from the group consisting of γ-glutamyl, α-glutamyl, β-aspartyl, α-aspartyl, β-alanine, 4-carboxy-phenylalanine, iminodiacetic acid, piperazine or aniline.

17. An insulin derivative or mixture of derivatives according to claim 1, wherein said derivative or mixture of derivatives is capable of forming water soluble, high-molecular-weight aggregates having a molecular weight>150 kDa.

18. A water soluble, protracted, glucose-dependent pharmaceutical composition comprising an insulin derivative or a mixture of insulin derivatives according to claim 1.

19. A soluble, long-acting, insulin preparation with a glucose-dependent release profile, comprising an insulin derivative or a mixture of insulin derivatives according to claim 1.

20. A soluble, biphasic-acting insulin preparation comprising (i) an insulin derivative according to claim 1 mixed with (ii) human insulin or an insulin with rapid onset of action.

21. A preparation according to claim 20, wherein said insulin with rapid onset of action is selected from the group consisting of des(B30) human insulin; Asp$^{B28}$ human insulin; Lys$^{B28}$Pro$^{B29}$ human insulin; Gly$^{A21}$,Lys$^{B3}$,Ile$^{B28}$ human insulin; Asp$^{A21}$,Lys$^{B3}$,Ile$^{B28}$ human insulin; Lys$^{B3}$Glu$^{B29}$ human insulin; Gly$^{A21}$Lys$^{B3}$Glu$^{B29}$ human insulin; Asp$^{A21}$Lys$^{B3}$Glu$^{B29}$ human insulin.

22. A preparation according to claim 20, wherein said (i) insulin derivative and (ii) human insulin or insulin with rapid onset of action are present in ratios from 10:1 to 1:10.

23. A soluble insulin composition comprising an insulin derivative according to claim 1, characterized by having a rate of absorption from an injected depot, which increases as the glucose concentration in the tissue increases, and decreases as the glucose concentration decreases.

24. A solid insulin composition comprising an insulin derivatives according to claim 1.

25. A method of treating diabetes in a patient in need of such a treatment, comprising administering to the patient a therapeutically effective amount of an insulin derivative according to claim 1.

26. An insulin derivative according to claim 13, wherein the polyol moiety is a derivative of D- or L-forms of glucamine, N-methyl-glucamine, galactamine, N-methyl-galactamine, mannamine, N-methyl-mannamine, gluconic acid, sorbitol, galactol, mannitol, quinic acid, shikimic acid, inositol, pinitol, tris(hydroxymethyl)-aminomethane, pentaerythritol, and derivatives of glucose, fructose, galactose, and mannose.

27. An insulin derivative according to claim 1, wherein the polyol moiety is a derivative of D- or L-forms of glucamine, N-methyl-glucamine, galactamine, N-methyl-galactamine, mannamine, N-methyl-mannamine, gluconic acid, sorbitol, galactol, mannitol, quinic acid, shikimic acid, inositol, pinitol, tris(hydroxymethyl)-aminomethane, pentaerythritol and their derivatives, or derivatives of glucose, fructose, galactose, mannose or other carbohydrates.

28. An insulin derivative according to claim 27, wherein the polyol moiety is a derivative of D- or L-forms of glucamine, N-methyl-glucamine, galactamine, N-methyl-galactamine, mannamine, N-methyl-mannamine, gluconic acid, sorbitol, galactol, mannitol, quinic acid, shikimic acid, inositol, pinitol, tris(hydroxymethyl)-aminomethane, pentaerythritol, and derivatives of glucose, fructose, galactose, and mannose.

29. An insulin derivative according to claim 1, wherein the derivative is selected from:

Lys$^{B29}$(N$^\epsilon$-(γ-L-glutamyl-α-D-glucamide, N$^\alpha$-(4-borono-benzoyl)) des(B30) human insulin;

Lys$^{B29}$(N$^\epsilon$-(γ-L-glutamyl-α-D-glucamide, N$^\alpha$-(3-borono-5-nitro-benzoyl)) des(B30) human insulin;

Lys$^{B29}$(N$^\epsilon$-(γ-L-glutamyl-α-(tris(hydroxymethyl)methylamide), N$^\alpha$-(4-borono-benzoyl)) des(B30) human insulin;

Lys$^{B29}$(N$^\epsilon$-(γ-L-glutamyl-α-(tris(hydroxymethyl)methylamide), N$^\alpha$-(3-borono-5-nitro-benzoyl)) des(B30) human insulin;

Lys$^{B29}$(N$^\epsilon$-(acetyliminoacet-N-methyl-glucamide), N-(4-borono-phenylsulfonyl)) des(B30) human insulin;

Lys$^{B29}$(N$^\epsilon$-(acetyliminoacet-N-methyl-glucamide), N-(3-borono-phenylsulfonyl)) des(B30) human insulin;

Lys$^{B29}$(N$^\epsilon$-4-carboxyphenylalanine-N-methyl-glucamide), N$^\alpha$-(4-borono-phenylsulfonyl)) des(B30), human insulin;

Lys$^{B29}$(N$^\epsilon$-(acetyliminoacet-N-methyl-glucamide), N-(3-borono-phenylsulfonyl)) des(B30) human insulin; and, Lys$^{B29}$(N$^\epsilon$-(γ-L-glutamyl-α-D-glucamide, N$^\alpha$-(3-borono-5-nitro-benzoyl)), B13Gln, human insulin.

* * * * *